US007819120B2

(12) United States Patent
Taylor et al.

(10) Patent No.: US 7,819,120 B2
(45) Date of Patent: Oct. 26, 2010

(54) RESPIRATORY COMPONENT MOUNTING ASSEMBLY

(75) Inventors: David S. Taylor, Accrington (GB); Peter D. Lee, Hartlepool (GB); Desmond T. Curran, Durham (GB); Peter B. Allen, Bracknell (GB); Scott R. Alexander, Reading (GB)

(73) Assignee: 3M Innovative Properties Company, St. Paul, MN (US)

( * ) Notice: Subject to any disclaimer, the term of this patent is extended or adjusted under 35 U.S.C. 154(b) by 1931 days.

(21) Appl. No.: 10/749,177

(22) Filed: Dec. 30, 2003

(65) Prior Publication Data

US 2005/0145251 A1 Jul. 7, 2005

(51) Int. Cl.

| | |
|---|---|
| *A62B 17/04* | (2006.01) |
| *A62B 7/10* | (2006.01) |
| *A62B 18/08* | (2006.01) |
| *A62B 18/02* | (2006.01) |
| *A62B 9/04* | (2006.01) |
| *A61M 16/00* | (2006.01) |
| *B42F 1/02* | (2006.01) |
| *A44B 1/04* | (2006.01) |

(52) U.S. Cl. ............................ 128/206.27; 128/206.16; 128/206.17; 128/206.18; 128/206.21; 128/206.23; 128/206.24; 128/206.26; 128/206.28; 128/207.11; 128/207.13; 128/207.17; 128/205.25; 128/201.22; 128/201.23; 128/201.24; 128/202.27; 24/545; 24/546

(58) Field of Classification Search ............ 128/206.16, 128/206.17, 206.18, 206.21, 206.23, 206.24, 128/206.26, 206.27, 206.28, 207.11, 207.13, 128/207.17, 205.25, 201.22, 201.23, 201.24, 128/202.27; 24/3.12, 545, 546

See application file for complete search history.

(56) References Cited

U.S. PATENT DOCUMENTS

| | | | |
|---|---|---|---|
| 5,052,603 | A | 10/1991 | Spina |
| 5,823,414 | A | 10/1998 | Gal et al. |
| 5,833,095 | A | 11/1998 | Russell et al. |
| 5,871,132 | A | 2/1999 | Hargreaves |

(Continued)

FOREIGN PATENT DOCUMENTS

| | | |
|---|---|---|
| DE | 8628812 | 1/1987 |
| GB | 1588993 | 5/1981 |
| GB | 2282407 | 4/1995 |
| WO | WO 96/28065 | 9/1996 |
| WO | WO 02/056966 | 7/2002 |

OTHER PUBLICATIONS

3M Jupiter Comfort Belt, Part No. 022-25-03P4 (first sold in 2001).
Hornell AdFlo7 powered respirator and belt, www.hornell.com/Regional/0/products/adflo (printed Sep. 16, 2003).

*Primary Examiner*—Patricia M Bianco
*Assistant Examiner*—Nihir Patel
(74) *Attorney, Agent, or Firm*—Anna A. Wetzels

(57) ABSTRACT

A respiratory component mounting assembly includes a first respiratory component, a second respiratory component and a mounting clip for mounting the second respiratory component to the first respiratory component. Each of the first and second respiratory components includes at least two spaced apart clip openings. The mounting clip has an intermediate portion and two spaced apart free ends connected to the intermediate portion. The intermediate portion of the mounting clip is received within both of the clip openings of the first respiratory component and the free ends of the mounting clip are received in the clip openings of the second respiratory component for releasably securing the first and second respiratory components together.

19 Claims, 22 Drawing Sheets

U.S. PATENT DOCUMENTS

| | | | |
|---|---|---|---|
| 5,954,250 | A | 9/1999 | Hall et al. |
| 6,003,744 | A | 12/1999 | Culjak et al. |
| 6,038,747 | A | 3/2000 | Hamilton et al. |
| 6,193,122 | B1 | 2/2001 | Buckley |
| 6,199,736 | B1 | 3/2001 | Musarella et al. |
| 6,206,257 | B1 | 3/2001 | Peele et al. |
| 6,575,165 | B1 | 6/2003 | Cook et al. |
| 6,907,882 | B2 * | 6/2005 | Ging et al. ............. 128/207.11 |

* cited by examiner

RESPIRATORY COMPONENT MOUNTING ASSEMBLY

BACKGROUND OF THE INVENTION

The present invention relates to a respiratory protection system. In particular, the invention concerns a waist-mounted respiratory component system including a mounting assembly for attaching a respiratory component to a belt.

Fan-forced positive pressure breathing apparatus, commonly known as Powered Air Purifying Respirators (PAPRs), and other respiratory components are used by first responders (HazMat, police, fire, and civil defense), military or other emergency response units to manage hazardous respiratory exposure. These respirators are generally used in industrial applications where the environmental hazards are well defined and quantified. Respiratory hazards might include harmful gases, vapors, and particulate matter. Respirators include a breathing mask, or other suitable hood, helmet or headtop, having a filtered air inlet. Respirators are employed to continually supply positive pressure to the wearer's mask. The filtered supplied air replenishes the internal confines of the mask and is continually ejected.

Currently, respiratory components are typically attached to a belt by threading the belt through slots in the housing of the respiratory component. The responder wears the belt carrying the respiratory components around his or her waist and the load is normally attached to the rear of the belt. In addition to carrying the respiratory component, the responder also wears or carries additional equipment, such as a hood, protective clothing, and protective footwear, some of which is also attached to the belt.

The attachment mechanism for securing the respiratory components to the belt should prevent the respiratory component from falling off the belt if caught on machinery or other apparatus while in use. In addition, the attachment mechanism should facilitate ease of attachment and detachment of the respiratory component to and from the belt. Current belt configurations and component attachment to those belts induce inefficient and cumbersome interchange of respiratory components carried by the belt. In order to remove a component and/or add a new component, the belt must be removed.

The respirators and associated components of the respiratory component system are generally exposed to hazardous environments, which cause contamination to those components, including any related attachment mechanisms for securing the respiratory components to the belt. Discarding contaminated equipment is costly and not desirable. Therefore, responders would prefer respiratory components and attachment mechanisms that may be decontaminated after each use, and then reused.

There exists a need for a waist-mounted respiratory protection system that is decontaminatible, and in particular, mounting assemblies for attaching respiratory components to a system belt. The mounting assemblies should be strong enough to secure the respiratory components to the belt without risk of the components falling off during use. In addition, the mounting assemblies should facilitate efficient attachment and detachment of a variety respiratory components.

BRIEF SUMMARY OF THE INVENTION

The present invention is directed to a respiratory component mounting assembly including a first respiratory component, a second respiratory component and a mounting clip. Each of the first and second respiratory components includes at least two spaced apart clip openings. The mounting clip has an intermediate portion and two spaced apart free ends connected to the intermediate portion. The intermediate portion of the mounting clip is received within both of the clip openings of the first respiratory component and the free ends of the mounting clip are received in the clip openings of the second respiratory component for releasably securing the first and second respiratory components together.

The present invention is also directed to a method for mounting a respiratory component to a user-wearable respiratory component support member. The method includes providing at least two spaced apart connector receptacles on the respiratory component, providing at least two slots in the support member, and providing a mounting clip having an intermediate portion and two spaced apart free ends projecting therefrom. The intermediate portion of the mounting clip is inserted into the slots on the support member, with the free ends of the mounting clip projecting from one side of the support member. The free ends of the mounting clip are inserted into the connector receptacles on the respiratory component.

In a further embodiment of the inventive method, the intermediate portion of the mounting clip is inserted into the clip openings on the respiratory component, with the free ends of the mounting clip projecting from one side of the respiratory component. The free ends of the mounting clip are then inserted into the slots of the support member.

BRIEF DESCRIPTION OF THE DRAWINGS

The present invention will be further explained with reference to the attached figures, wherein like structure is referred to by like numerals throughout the several views.

While the above-identified drawing figures set forth several embodiments of the invention, other embodiments are also contemplated, as noted in the discussion. In all cases, this disclosure presents the present invention by way of representation and not limitation. It should be understood that numerous other modifications and embodiments can be devised by those skilled in the art which fall within the scope and spirit of the principles of this invention.

DETAILED DESCRIPTION

Figure 1:
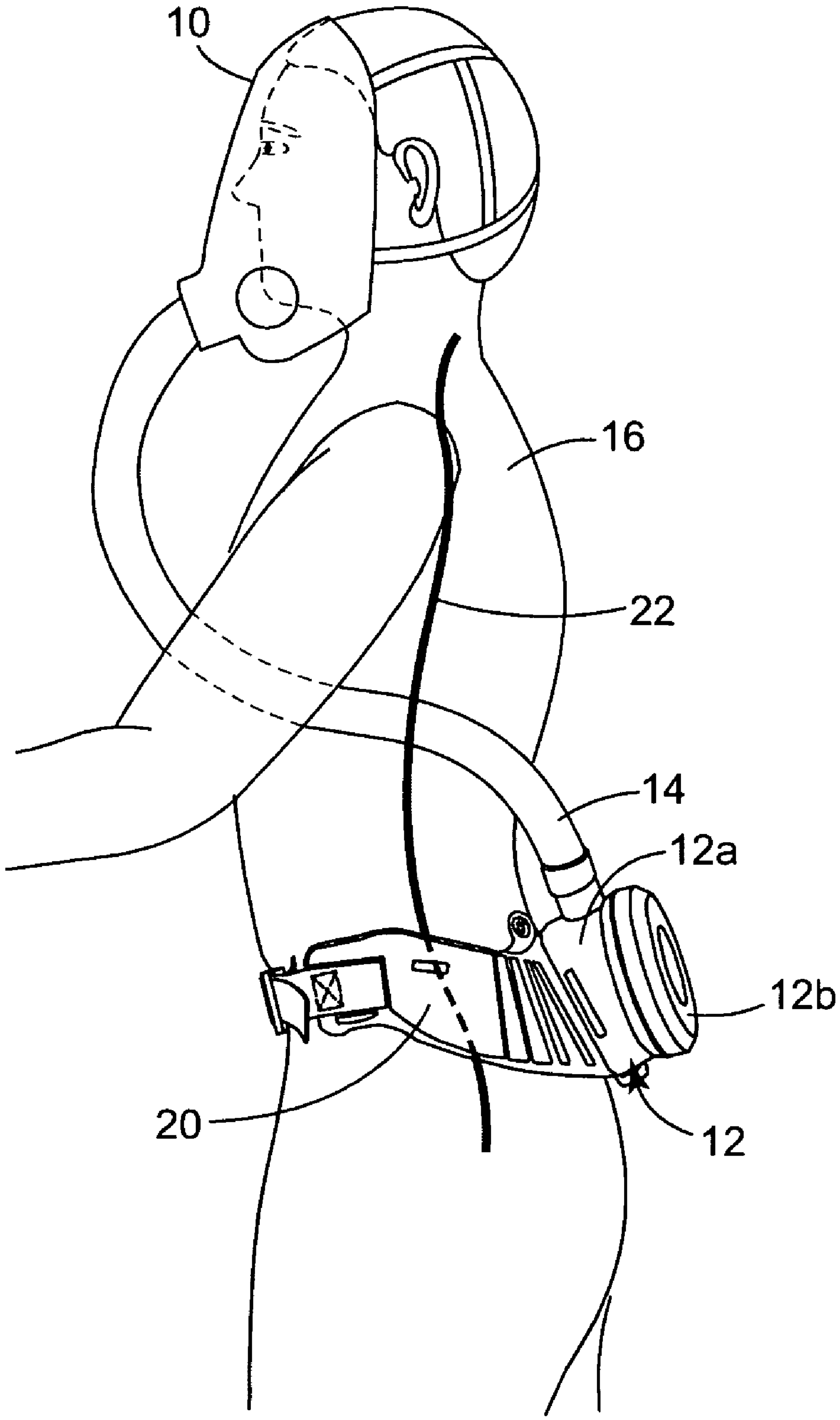
FIG. 1 is an illustration of a respiratory protection system worn by a user.

A respiratory protection system worn by a user is shown in FIG. 1. The respiratory protection system includes a breathing face-piece 10, or head gear, and a respiratory component 12, such as a fan-forced positive pressure breathing device, commonly known as a Powered Air Purifying Respirator (PAPR), an air filter or some other component device which may be used in a respiratory system, such as an air quality monitor. An air hose or tube 14, connects the respiratory component 12 to the breathing face-piece 10 to supply breathable air to a user 16. The respiratory component 12 is designed to be worn by a user working an atmosphere with unwanted contaminants, including respiratory hazards. The PAPR 12 has a housing 12*a* and one or more filter units 12*b*, which serve to filter unwanted contaminants from the surrounding atmosphere, thus allowing a user wearing the PAPR to work in contaminated or hazardous areas. One example of a PAPR is disclosed and described in U.S. Pat. No. 6,575,165, entitled "Apparatus and Method for Breathing Apparatus Component Coupling."

The present invention concerns a respiratory component mounting assembly 18 (shown in FIG. 2) for attaching the respiratory component to a belt 20, which is a user-wearable respiratory component support member. The belt 20 may be used with a variety of respiratory components 12 for hands-free use in contaminated areas. The respiratory component 12 is attached to the belt 20 for carrying by the user 16 and positioned such that the load is carried at the rear of the belt 20.

The respiratory component 12 attached to the belt 20 allows carriage by the user 16 of the respiratory component 12 with the hands left free for other purposes. In addition, the belt 16 is configured to provide an anatomical fit wherein the hips carry the load of the respiratory component 12, leg movement is freed, and the lumbar of the back is firmly supported. The belt 20 also cushions the back of the user 16 while still maintaining rigidity to support the respiratory component 12. Line 22 represents the curvature of a user's spine. The respiratory component 12 is formed from a decontaminatible material such that after use in hazardous areas, the belt 20 may be decontaminated for future reuse.

Figure 2:
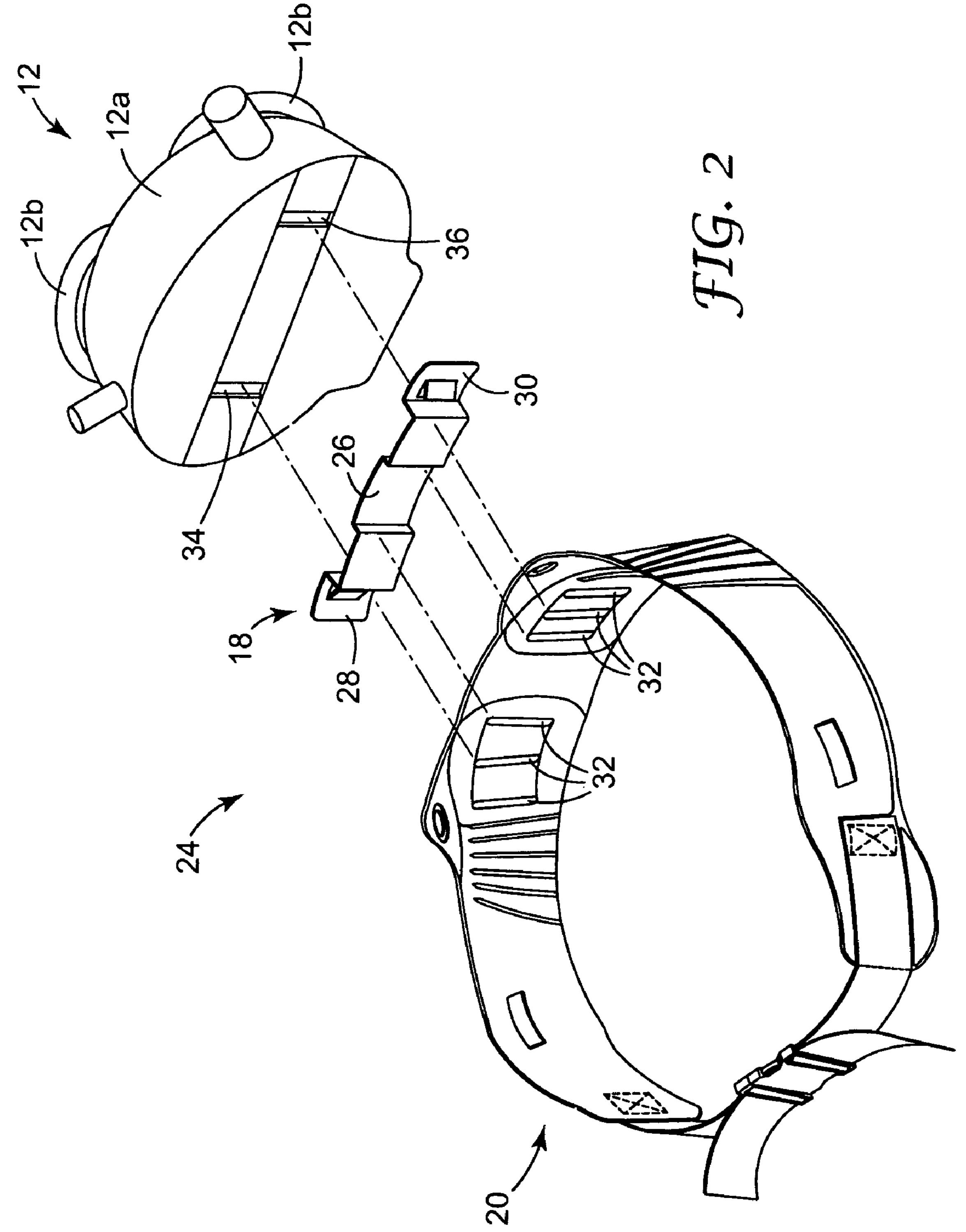
FIG. 2 is an exploded perspective view of a waist-mounted respiratory component system.

FIG. 2 is an exploded perspective view of a waist-mounted respiratory component system 24. The waist-mounted respiratory component system 24 includes the belt 20, the mounting assembly 18 for mounting the respiratory component 12 to the belt 20, and the respiratory component 12. The mounting assembly 18 includes an intermediate portion 26 and two spaced apart free ends 28, 30 connected to the intermediate portion 26. The belt 20 includes spaced apart mounting slots 32, or clip openings, for attaching the mounting assembly 18 to the belt 20. The mounting slots 32 receive the intermediate portion 26 of the mounting assembly 18, for example, the mounting assembly 18 is woven through the mounting slots 32 of the belt 20. The respiratory component 12 includes two spaced apart openings, 34, 36 or connector receptacles, that receive the free ends 28, 30 of the mounting assembly 18 for releasably securing the respiratory component 12 to the belt 20. In further embodiments of the respiratory component system 24, the mounting slots 32 of the belt receive the free ends 28, 30 of the mounting assembly 18 and the openings 34, 36 of the respiratory component 12 receive the intermediate portion 26 of the mounting assembly 18. Although the mounting slots 32 and clip openings 34, 36 shown in FIG. 2 are generally parallel and vertically aligned, those skilled in the art will recognize that other configurations and orientations for the slots and openings are possible. U.S. patent application Ser. No. 10/748,907, entitled "Anatomically Fitted Respiratory Component Belt" and filed on the same date herewith, discusses the belt 18 in further detail and is incorporated herein by reference.

Figure 3:
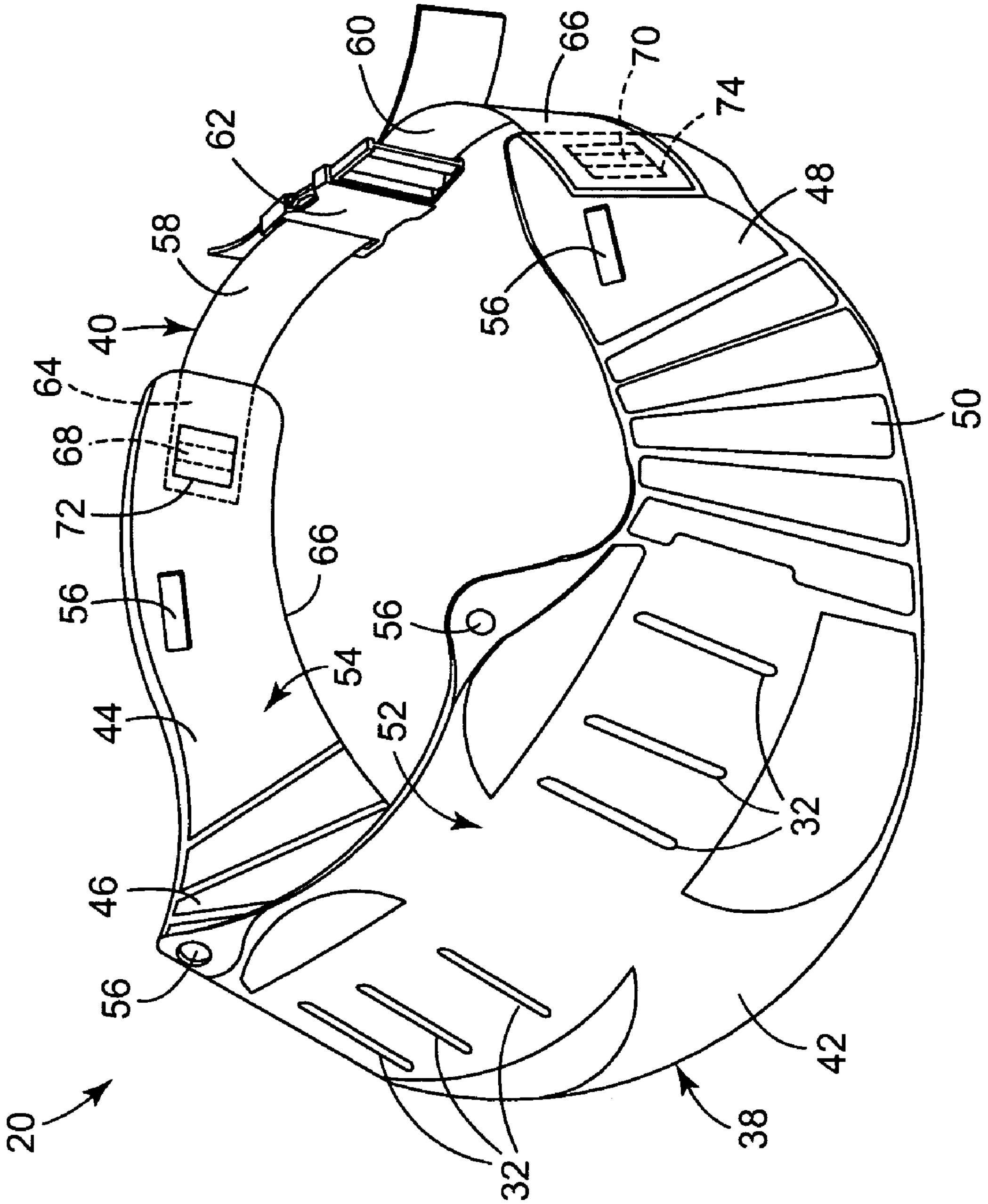
FIG. 3 is a perspective view of a belt for carrying one or more waist-mounted respiratory protection components.
Figure 4:
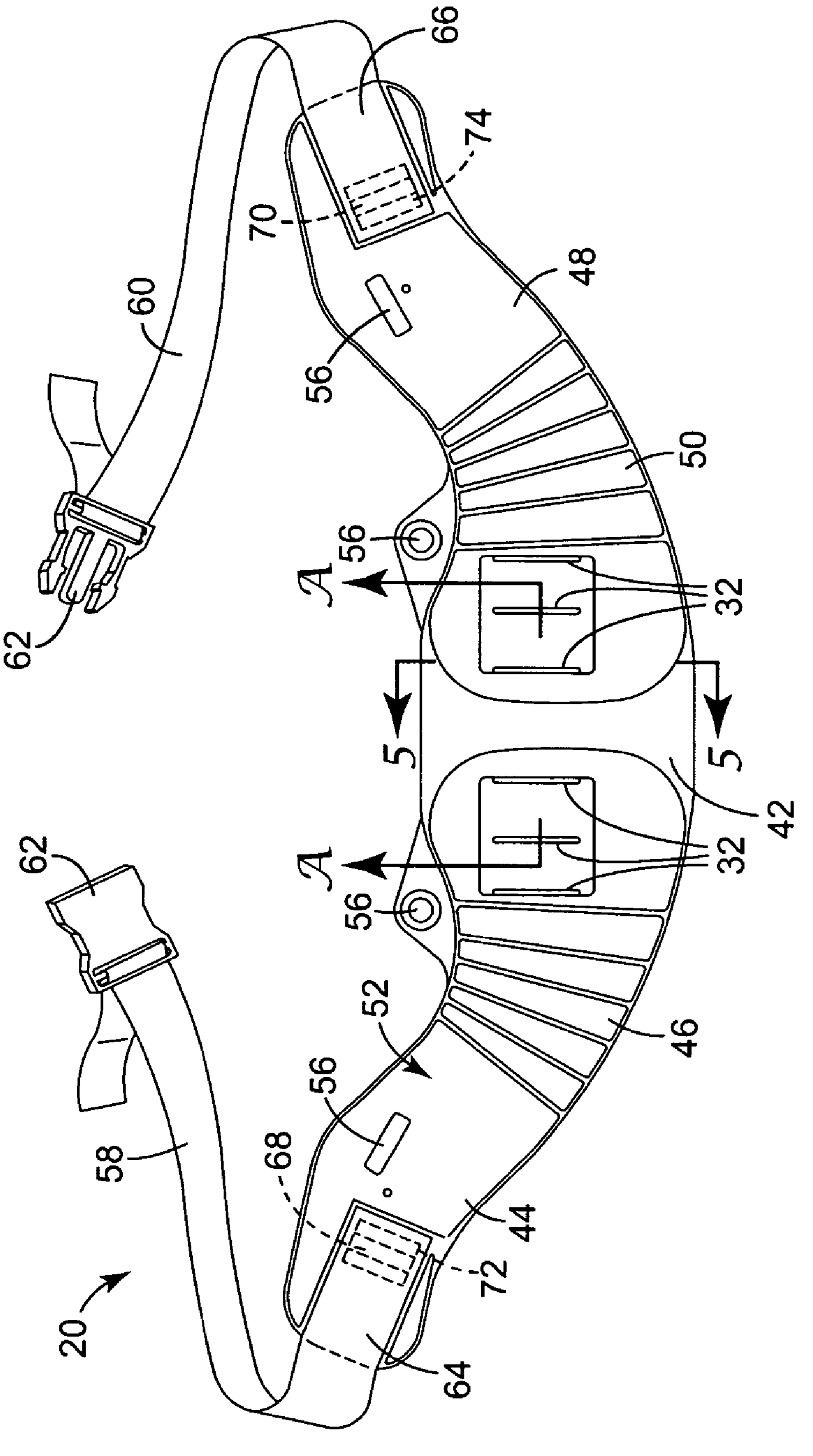
FIG. 4 is a perspective view of the belt of the waist-mounted respiratory component system.
Figure 5:
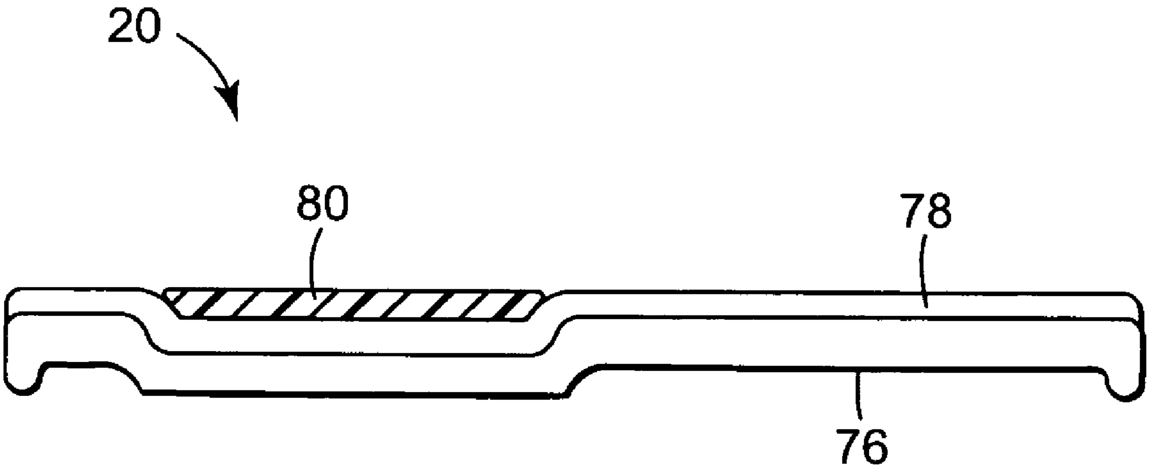
FIG. 5 is a cross-sectional view of the belt taken along line 5-5 of FIG. 4.
Figure 6:
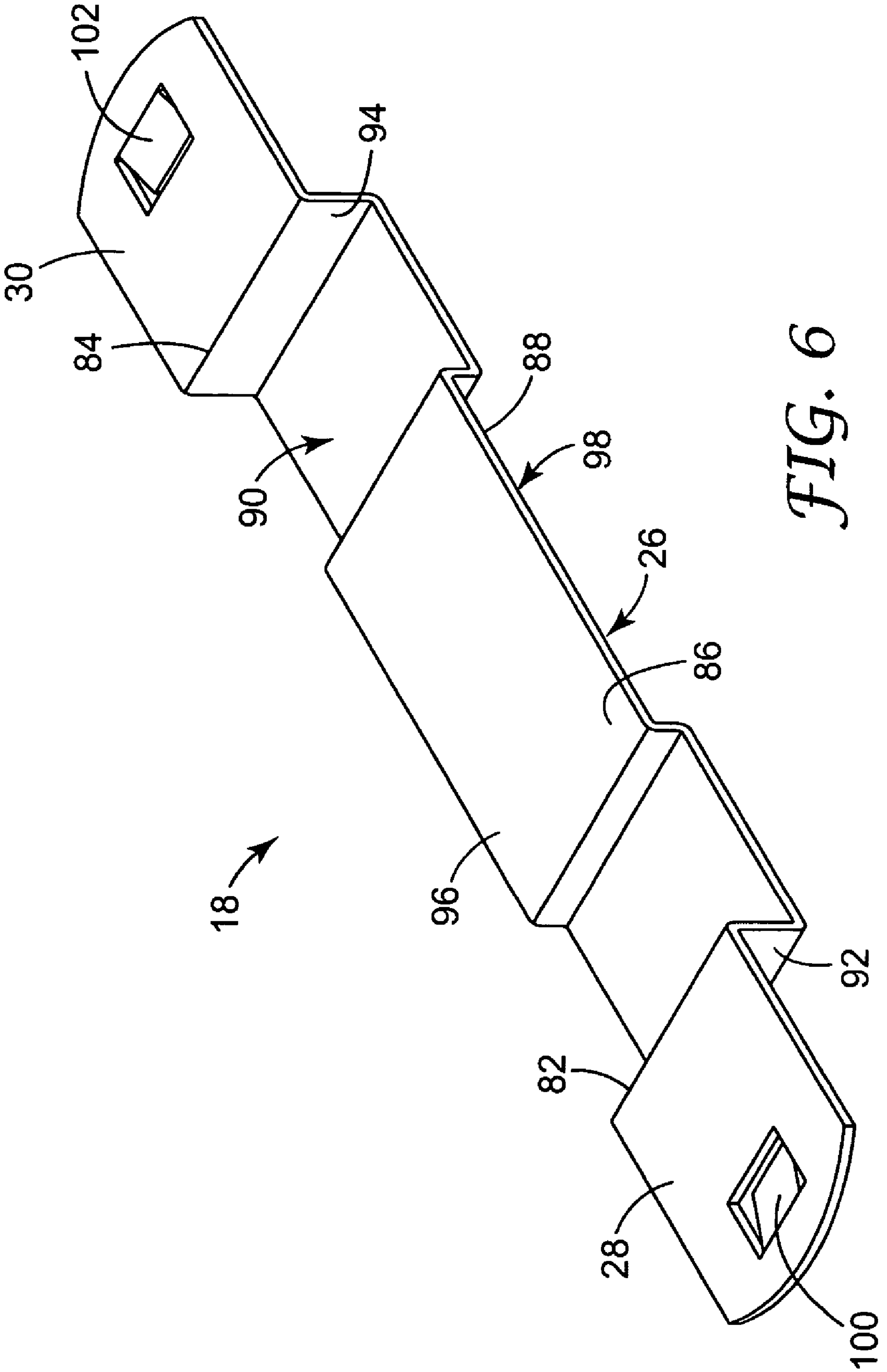
FIG. 6 is a perspective view of a respiratory component mounting clip.
Figure 7:
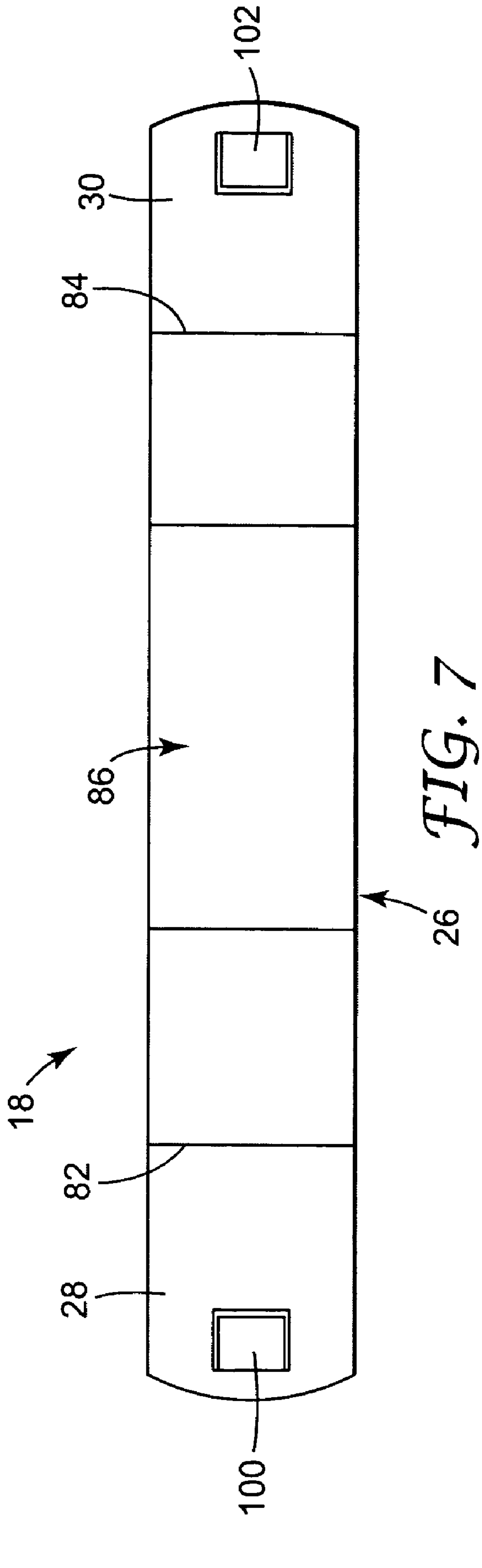
FIG. 7 is a top view of the respiratory component mounting clip of FIG. 6.
Figure 8:
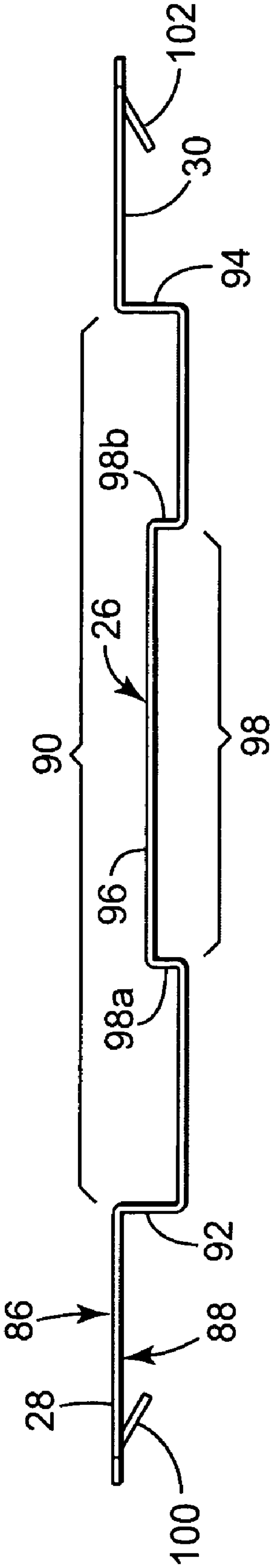
FIG. 8 is a side view of the respiratory component mounting clip of FIG. 6.

FIGS. 3-5 show an embodiment of the respiratory protection system belt 20. FIG. 3 provides a perspective view of the belt 20, while FIG. 4 is a front perspective view of the belt 20 and FIG. 5 is a cross-sectional view of the belt 20 taken along lines 5-5 of FIG. 4. The belt 20 for carrying one or more respiratory components 12 includes a main belt portion 38, which extends around the back and sides of a user, and a belt buckle portion 40, which extends across a front of a user. The main belt portion 38 includes a back section 42, a left side section 44, a left connective section 46 between the back section 42 and the left side section 44, a right side section 48 and a right connective section 50 between the back section 42 and the right side section 48. The main belt portion 38 includes an outer face 52 and an inner face 54. The back section 42 is wider than the other sections of the main belt portion 38. The left and right side sections 44, 48 and the left and right connective sections 46, 50 are symmetrically shaped relative to the back section 42.

The back section 42 includes two sets of mounting slots, each comprised of three slots 32. Those skilled in the art will recognize that further embodiments of the belt may include fewer or more mounting slot sets comprised of fewer or more slots. The slots 32 are used for mounting the respiratory component 12 to the belt 20, and in particular, for receiving the mounting assembly 18. The main belt portion 38 includes connector elements 56 for use in mounting additional supportive or respiratory components to the belt 20.

In use, the main belt portion 38 has a substantially conical shape such that the belt 20 secures around a user's pelvic girdle and aligns the respiratory component 12 thereon over the lumbar region of a user's spine. The belt 20 distributes the weight of the respiratory component 12 around a user's pelvis such that a user's hips carry the load of the respiratory component 12. In addition, the shape and the position of the main belt portion 38 allows free leg movement of the user and minimizes pinching adjacent a user's iliac crests during such movement. The position of the main belt portion 38 with respect to a user's spine shifts the rotational momentum of the weight of the respirator component 12 to the user. Overall, the shape of the main belt portion 38 of the belt 20 facilitates positioning of the respiratory component 12, while the belt 20 is worn by a user, over a user's lumbar region at an angle of inclination to enhance comfort of a user.

The belt buckle portion 40 of the belt 20 includes a left piece 58 connected to the left side section 44 of the main belt portion 38 and a right piece 60 connected to the right side section 48 of the main belt portion 38. Each piece 58, 60 of the belt buckle portion 40 is adjustable in length, although in further embodiments of the belt 20 only one piece may be adjustable. Free ends of the left and right pieces are selectively connected together by a buckle 62, such as a releasable buckle, or any other buckle known in the art. In one embodiment, first ends 64, 66 of the left and right pieces 58, 60 of the belt buckle portion 40 are fixedly connected (for example, by stitching or adhesive) to the main belt portion 38. Alternatively, first ends 64, 66 may be detachably connected to the respective left and right side sections 44, 48. In this case, each side section 44, 48 includes an opening 68, 70 for receiving the first end of the respective belt piece and the first end of each belt piece includes a hinged connective member 72, 74. To attach or release either belt piece 58, 60 from the main belt portion 38, the connective member 72, 74 folds at its hinge to narrow the connective member 72, 74 to facilitate sliding of the connective member 72, 74 through the opening 68, 70 of the side section 44,48. In an attached position, the connective member 72, 74 is unfolded at the hinge such that the connective member 72, 74 is wider than the opening 68, 70 to prevent removal of the belt piece 58, 60 from the main belt portion 38. Those skilled in the art will recognize that there are other possible means for releasably connecting belt buckle portion 40 to main belt portion 38.

As shown in FIG. 5, the main belt portion 38 has an outer layer 76 and an inner layer 78. The outer layer 76 provides rigidity and the inner layer 78, which contacts a user's body, provides a cushioning layer. The slots 32 in the back section 42 of the main belt portion 38 are reinforced with a reinforcement member 80, such as a plate. The reinforcement member 80 stabilizes the respiratory component 12 and prevents separation of the respiratory component 12 and the mounting assembly 18 or the belt 20, and movement of the respiratory component away from the belt 20.

Both the outer layer 76 and the inner layer 78 of the main belt portion 38 are formed from an ethyl vinyl acetate (EVA) co-polymer with a polyolefin elastomer. One suitable EVA is made by Alveo (a Sekisui Company of Luzern, Switzerland). The outer layer 76 EVA has a density of about 125 $kg/m^3$ and the inner layer 78 EVA has a density of about 70 $kg/m^3$ to about 75 $kg/m^3$. Thereby the outer layer 76 is more rigid than the inner layer 78 to form a rigid support piece, whereas the inner layer 78 is less rigid to provide more comfort to a user. The reinforcement member 80 is formed from a low density polyethylene such as made by VTS Plastics (Liverpool, UK). The belt buckle portion 40 is formed from a polyester coated with polyurethane or PVC, which allows the belt buckle portion 40 to be wiped clean.

FIGS. 6-9 further illustrate one embodiment of the inventive mounting assembly 18, a mounting clip, shown in FIG. 2, for attaching the respiratory component 12 to the belt 20. The mounting clip 18 includes the intermediate portion 26 and two spaced apart free ends 28, 30 connected to the intermediate portion 26. The intermediate portion 26 extends between a first shoulder 82 and a second shoulder 84, while the first and second free ends 28, 30 extend from the first and second shoulders 82, 84, respectively. The free ends 28,30 are aligned to extend in generally opposite directions. The mounting clip 18 has a first surface 86 and a second surface 88.

The first surface 86 of the intermediate portion 26 defines a channel 90 extending between a first outer wall 92 and a second outer wall 94. The channel 90 includes a stepped portion 96 extending towards the first surface 86 and defining a second channel 98 on the second surface 88 of the mounting clip 18. A depth of the first channel 90 (defined by walls 92 and 94) is greater than a depth of the second channel 98 (defined by walls **98*a* and 98*b*). The first and second free ends 28, 30 of the mounting clip 18 include first and second biased detent tabs 100, 102 extending generally downwardly and inwardly from the second surface 88 of the mounting clip 18**.

Figure 9:
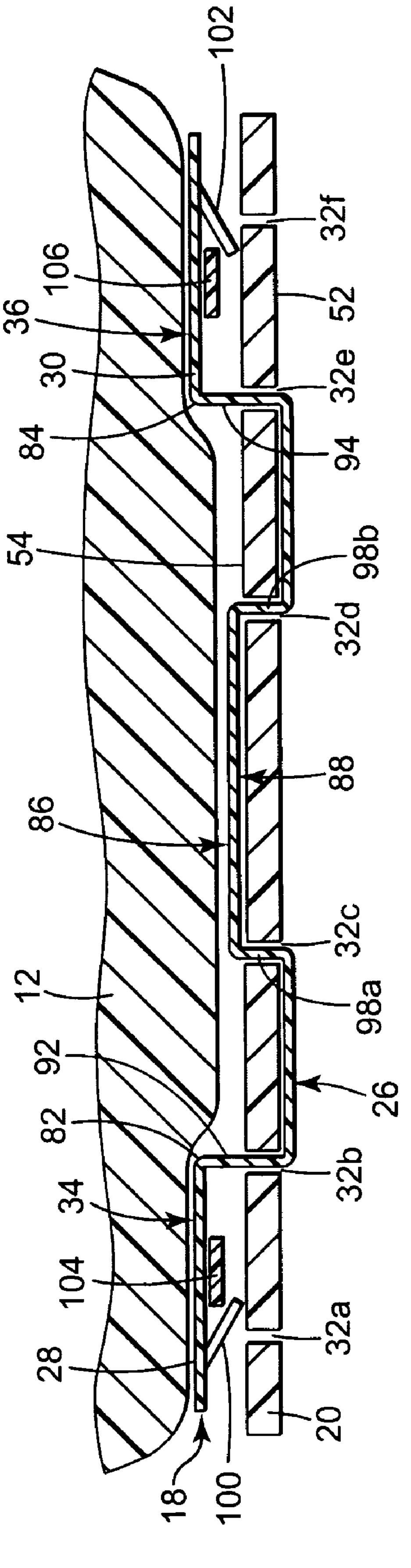
FIG. 9 is a schematic cross-sectional view of the waist-mounted respiratory component system, taken along line A-A of FIG. 4, and including the respiratory component mounting clip of FIG. 6.

FIG. 9 is a schematic cross-sectional view of the waist-mounted respiratory component system 24, taken along line A-A of FIG. 4, showing the respiratory component mounting clip 18 and the respiratory component 12 mounted to the belt 20. An example of a suitable respiratory component for use with the mounting clip 18 is JUPITER brand respirator from 3M Company of St. Paul, Minn. The intermediate portion 26 of the clip 18 is woven through the mounting slots 32 of the belt 20, whereby the free ends 28, 30 project from the inner face 54 of the belt 20. In the embodiment shown in FIG. 9, four of the mounting slots **32*b*, 32*c*, 32*d* and 32*e* receive walls 92, 98*a*, 98*b* and 94, respectively, of the intermediate portion 26 of the clip 18. Between each adjacent mounting slot 32*b*, 32*c*, 32*d* and 32*e*, one of the two faces (86, 88) of the clip 18 aligns against either the outer face 52 or the inner face 54 of the belt 20. The respiratory component 12 includes first and second openings 34, 36 for removably receiving the free ends 28, 30 of the clip. The respiratory component 12 also includes first and second opposed detent surfaces 104, 106 adjacent the first and second clip openings 34, 36, respectively. The openings 34, 36 of the respiratory component 12 receive the free ends 28, 30 of the clip 18 whereby the detent tabs 100, 102 of the clip 18 form a locking engagement with the detent surfaces 104, 106 of the respiratory component 12, as seen in FIG. 9**.

The mounting assembly 18 firmly secures the respiratory component 12 to the belt 20 and prevents the respiratory component 12 from falling off the belt 20 during normal use, and provides strong enough attachment to prevent separation of the respiratory component 12 from the belt 20 even if caught on machinery or other apparatus. The mounting assembly 18 provides easy attachment and detachment of the respiratory component 12 to and from the belt 20 and facilitates efficient interchange between respiratory components carried by the belt. To attach or remove the respiratory component 12 from the belt 20, the free ends 28, 30 of the clip 18 are inserted into or removed from the clip openings 34, 36 in the respiratory component 12. Detent tabs 100 and 102 are pressed towards the second surface 88 of the clip 18 to facilitate insertion and removal of the clip from the respiratory component. At least the free ends 28, 30 of the clip 18 are flexibly resilient to accommodate insertion and removal to and from the clip openings 34, 36 of the respiratory component 12. The intermediate portion 26 of the clip 18 is sufficiently flexible to weave through the mounting slots 32 of the belt 20.

FIGS. 10-13 illustrate a further embodiment of the inventive mounting assembly, a mounting clip 110, for attaching a respiratory component 12 to the belt 20. The mounting clip 110 includes an intermediate portion 112 and two spaced apart first and second free ends 114, 116 connected to the intermediate portion 112. The mounting clip has a first surface 118 and a second surface 120. The intermediate portion 112 extends between a first pair of living hinges 122 and a second pair of living hinges 124, which connect the intermediate portion 112 to the first and second free ends 114, 116, respectively.

Figure 10:
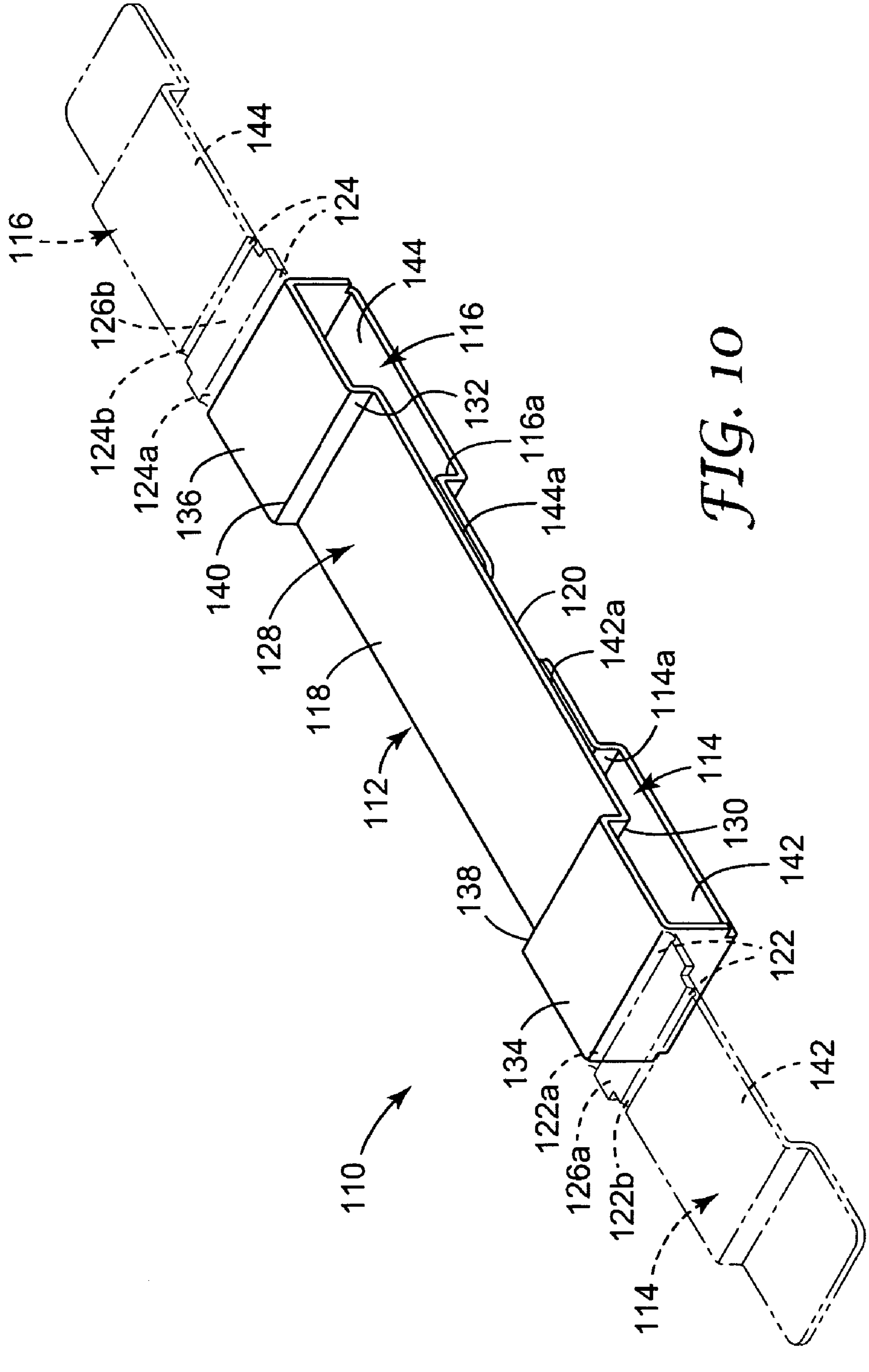
FIG. 10 is a perspective view of a further embodiment of a respiratory component mounting clip.
Figure 11:
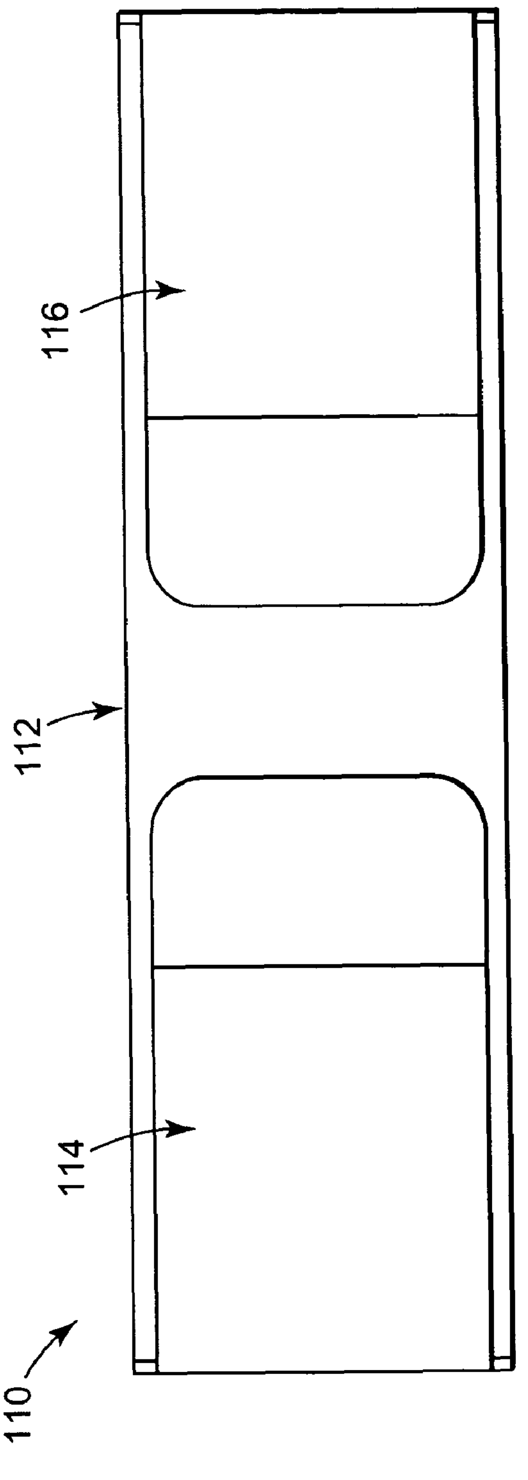
FIG. 11 is a bottom view of the respiratory component mounting clip of FIG. 10.
Figure 12:
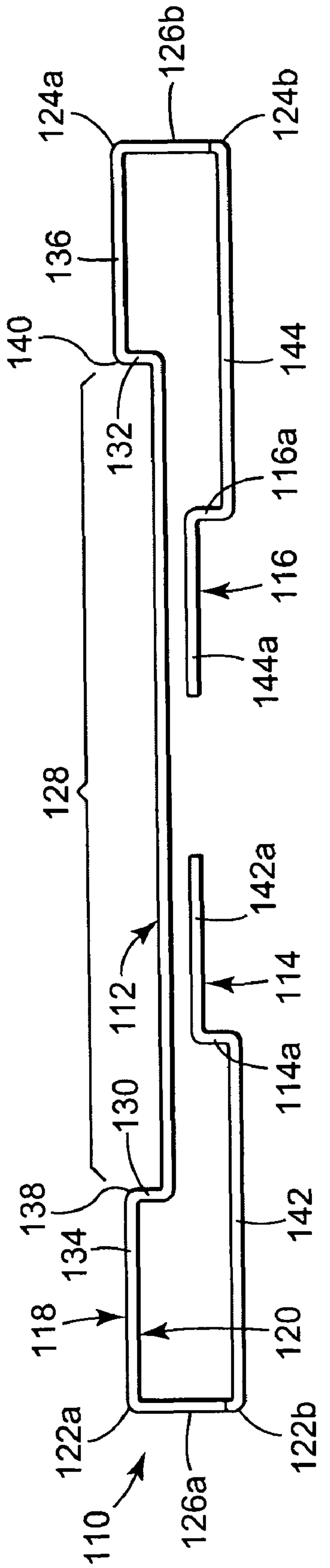
FIG. 12 is a side view of the respiratory component mounting clip of FIG. 10.

The free ends 114, 116 of the mounting clip 110 fold and extend, at the living hinges 122, 124, between a folded, use position (shown in solid lines in FIG. 10) and an extended position (shown in broken lines in FIG. 10). In the use position, the free ends 114, 116 are aligned to extend toward each other and the second surface 120 of the intermediate portion 112 and the free ends 114, 116 are aligned generally horizontally relative to the intermediate portion 112. Each pair of living hinges 122, 124 includes an upper hinge 122*a*, 124*a* and a lower hinge 122*b*, 124*b* spaced apart and separated by a connector wall 126*a*, 126*b*.

The first surface 118 of the intermediate portion 112 defines a channel 128 extending between a first channel wall 130 and a second channel wall 132. The intermediate portion 112 also includes first and second intermediate ledges 134, 136. The first intermediate ledge 134 extends from a first shoulder 138 adjacent the first channel wall 130 to the first, upper living hinge 122*a*. The second intermediate ledge 136 extends from a second shoulder 140 adjacent the second channel wall 132 to the second, upper living hinge 124*a*. Each free end 114, 116 is stepped, as at stepped walls 114*a* and 116*a*, and includes an end ledge 142, 144 generally parallel and horizontally aligned with its respective intermediate ledge 134, 136, when the free ends 114, 166 are in the extended position. Each free end 114 and 116 also includes an outermost free ledge 142*a* and 144*a*, respectively, extending beyond stepped walls 114*a* and 116*a*.

Figure 13:
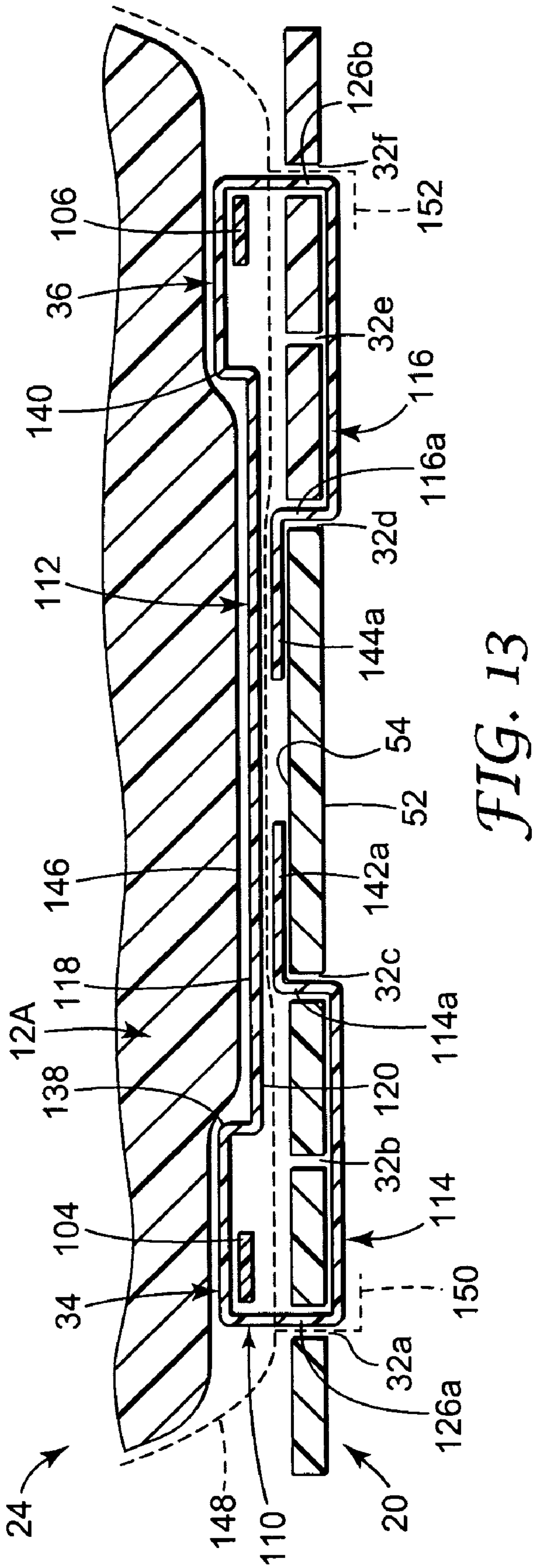
FIG. 13 is a schematic cross-sectional view of the waist-mounted respiratory component system, taken along line A-A of FIG. 4, and including the respiratory component mounting clip of FIG. 10.

FIG. 13 is a cross-sectional view of the waist-mounted respiratory component system 24 taken along line A-A of FIG. 4, showing the respiratory component mounting clip 110 and another respiratory component 12A mounted to the belt 20. An example of a suitable respiratory component for use with the mounting clip 110 is JUPITER brand respirator from 3M Company of St. Paul, Minn. First and second clip openings 34, 36 of the respiratory component 12 receive the intermediate portion 112 of the clip 110. The openings 34, 36 of the respiratory component 12A receive the intermediate portion 112 of the clip 110 whereby the intermediate portion 112 is woven through the openings 34, 36 and passes along an outer wall 146 of the respiratory component 12A. The free ends 114, 116 of the clip 110 are woven through the mounting slots 32 of the belt 20, whereby the end ledges 142 and 144 of the free ends 114, 116 project along the outer face 52 of the belt 20, while the outermost free ledges 142*a*, 144*a* project along the inner face 54 of the belt 20. In the embodiment shown in FIG. 13, four of the mounting slots 32*a*, 32*c*, 32*d* and 32*f* receive the walls 126*a*, 114*a*, 116*a* and 126*b*, respectively, of free ends 114, 116 of the clip 110. Between each mounting slot 32, one of the two surfaces (118, 120) of the clip 110 aligns against either the outer face 52 or the inner face 54 of the belt 20. To attach or remove the respiratory component 12 from the belt 20, the free ends 114, 116 of the clip 110 are inserted into or removed from the mounting slots 32 in the belt 20. At least the free ends 114, 116 of the clip 18 are flexibly resilient to accommodate insertion and removal to and from the mounting slots 32 of the belt 20. The intermediate portion 112 of the clip 110 is sufficiently flexible to weave through the clip openings 34, 36 of the respiratory component 12A.

Figure 14:
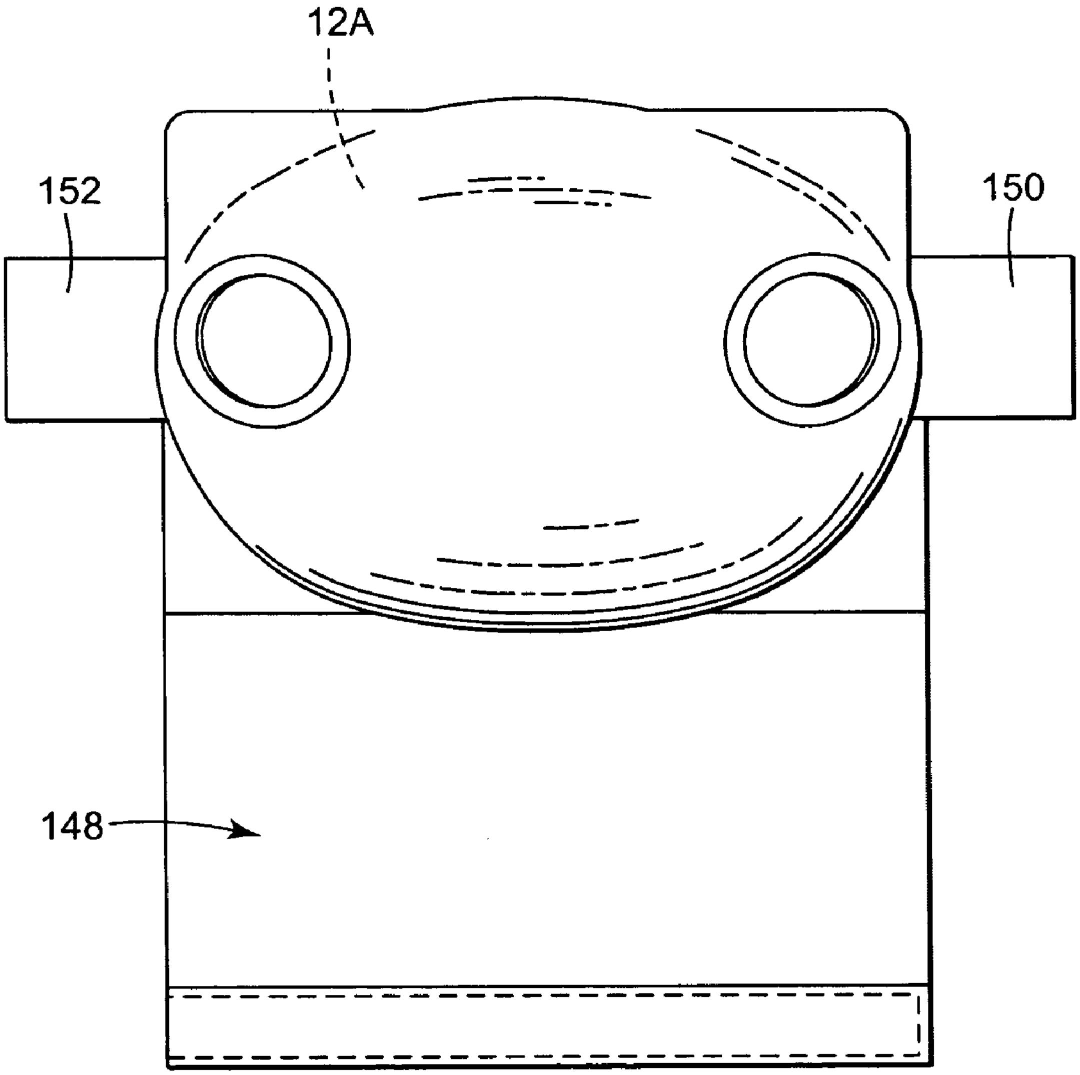
FIG. 14 is a side view of a respiratory component encased in a protective pouch.
Figure 15:
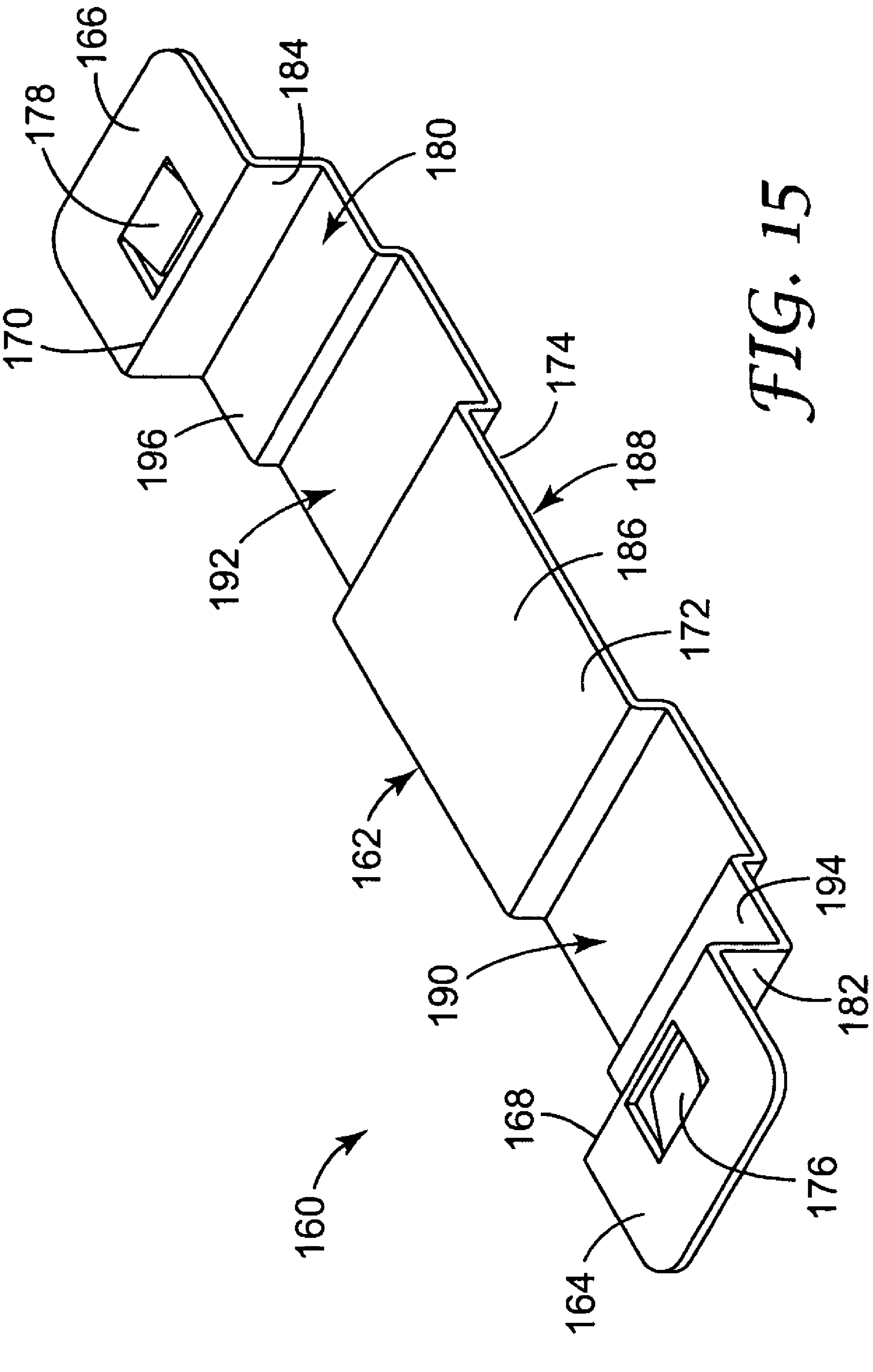
FIG. 15 is a perspective view of a further embodiment of a respiratory component mounting clip.
Figure 16:
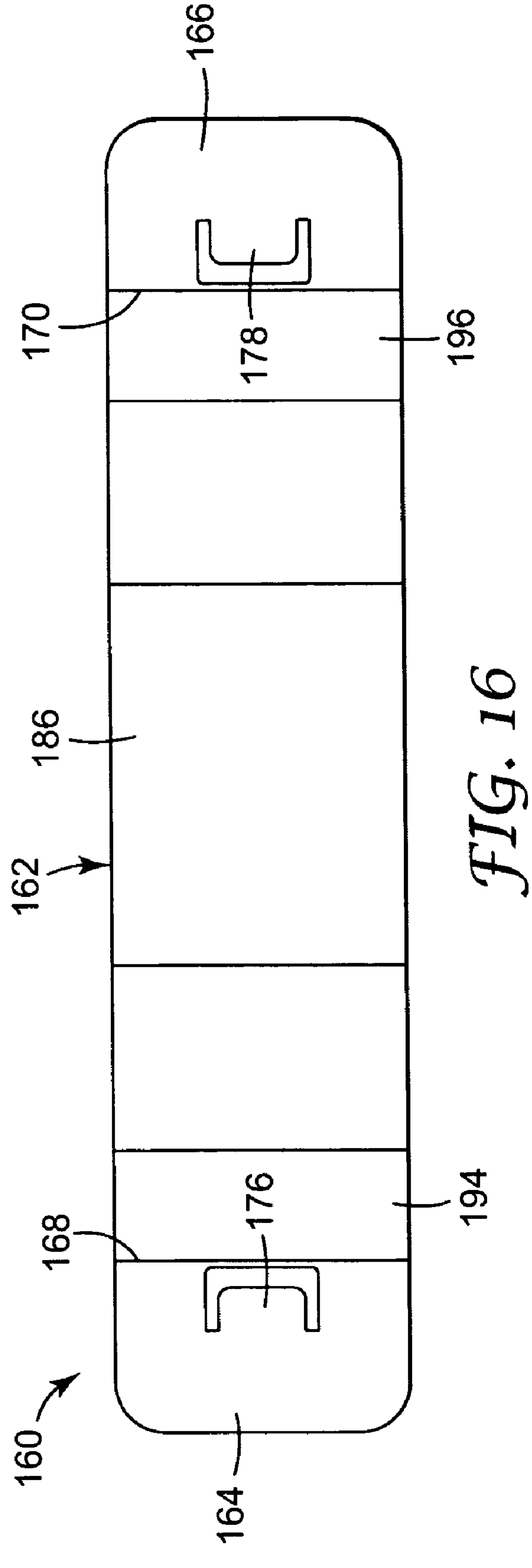
FIG. 16 is a top view of the respiratory component mounting clip of FIG. 15.
Figure 17:
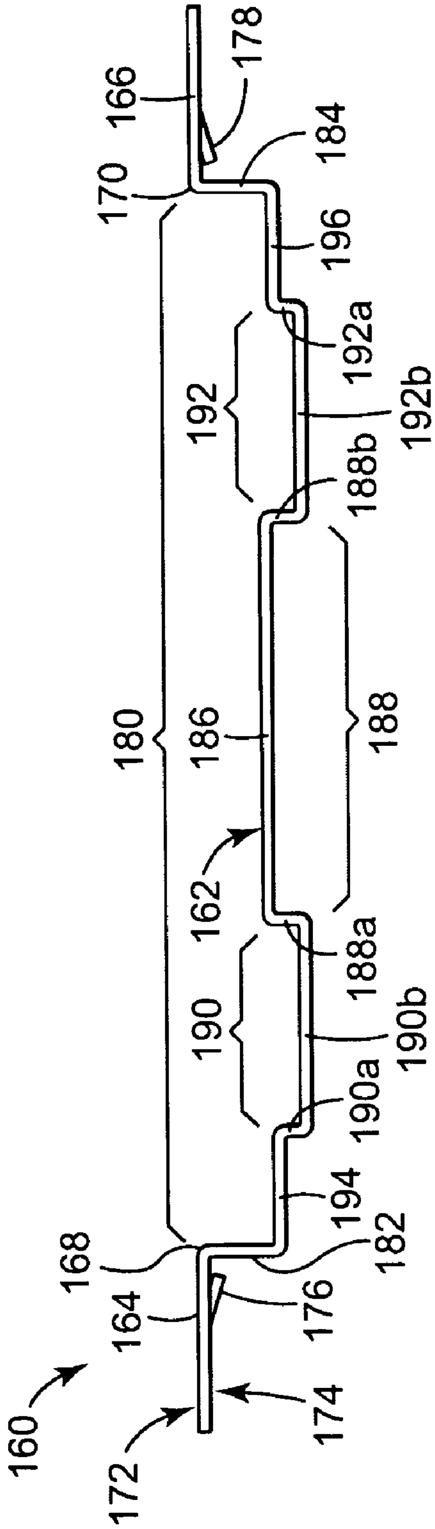
FIG. 17 is a side view of the respiratory component mounting clip of FIG. 15.

The mounting assembly 110 shown in FIGS. 10-13 is particularly useful in explosive or dusty environments. As seen in FIG. 14, a protective pouch 148 can be used to encase the respiratory component 12 to keep dust out of the component and/or prevent explosive materials from coming into contact with the component. FIG. 14 is a side view of the respiratory component 12A encased in the protective pouch 148. In FIG. 13, the protective pouch 148 is shown in phantom. An example of a suitable protective pouch for use with the mounting clip is JUPITER IS brand protective pouch from 3M Company of St. Paul, Minn.

The respiratory component 12A is placed in the protective pouch 148 and the intermediate portion 112 of the mounting clip 110 is inserted through the openings 34, 36 on the respiratory component 12. The pouch 148 includes sleeves 150, 152 for free ends 114 and 116 of the mounting clip 110 to pass through. The free ends 114, 116 of the mounting clip 110 project through the pouch 148 while the intermediate portion 110 is enclosed within the pouch 148. Because the free ends 114, 116 are received by the belt 20 (rather than the respiratory component 12), the respiratory component 12A is enclosed in the pouch 148, yet still detachable from the belt 20 without exposing the respiratory component 12A to a harmful environment. In further applications of the mounting assembly 110, the respiratory component 12A is not encased in the protective pouch 148.

FIGS. 15-18 illustrate a further embodiment of the inventive mounting assembly, a mounting clip 160, for attaching a respiratory component 12 to the belt 20. The mounting clip 160 includes an intermediate portion 162 and two spaced apart free ends 164, 166 connected to the intermediate portion 162. The intermediate portion 162 extends between a first shoulder 168 and a second shoulder 170, while the first and second free ends 164, 166 extend from the first and second shoulders 168, 170, respectively. The free ends 164, 166 are aligned to extend in generally opposite directions. The mounting clip 160 has a first surface 172 and a second surface 174. The first and second free ends 164, 166 of the mounting clip 160 include first and second biased detent tabs 176, 178 extending generally downwardly and inwardly from the second surface 174 of the mounting clip 160.

The first surface 172 of the intermediate portion 162 defines a channel 180 extending between a first outer wall 182 and a second outer wall 184. The channel 180 includes a stepped portion 186 extending towards the first surface 172 and defining a second channel 188 on the second surface 174 of the mounting clip 160. A depth of the first channel 180 (defined by walls 182 and 184) is greater than a depth of the second channel 188 (defined by walls 188*a* and 188*b*). Formed in the channel 180 are first and second subchannels

190, 192, which extend towards the second surface 174 and are defined on the first surface 172 of the mounting clip 160. A depth of each subchannel 190 (defined by walls 190*a* and 188*a*) and 192 (defined by walls 192*a* and 188*b*) is substantially equal to the depth of the second channel 188. First and second ledges 194, 196 extend between the first and second subchannels 190, 192 and the first and second outer walls 182, 184, respectively. Ledge 190*b* is in the subchannel 190, ledge 192*b* is in the subchannel 192, and the stepped portion 186 is in the channel 188 and separates subchannels 190 and 192.

Figure 18:
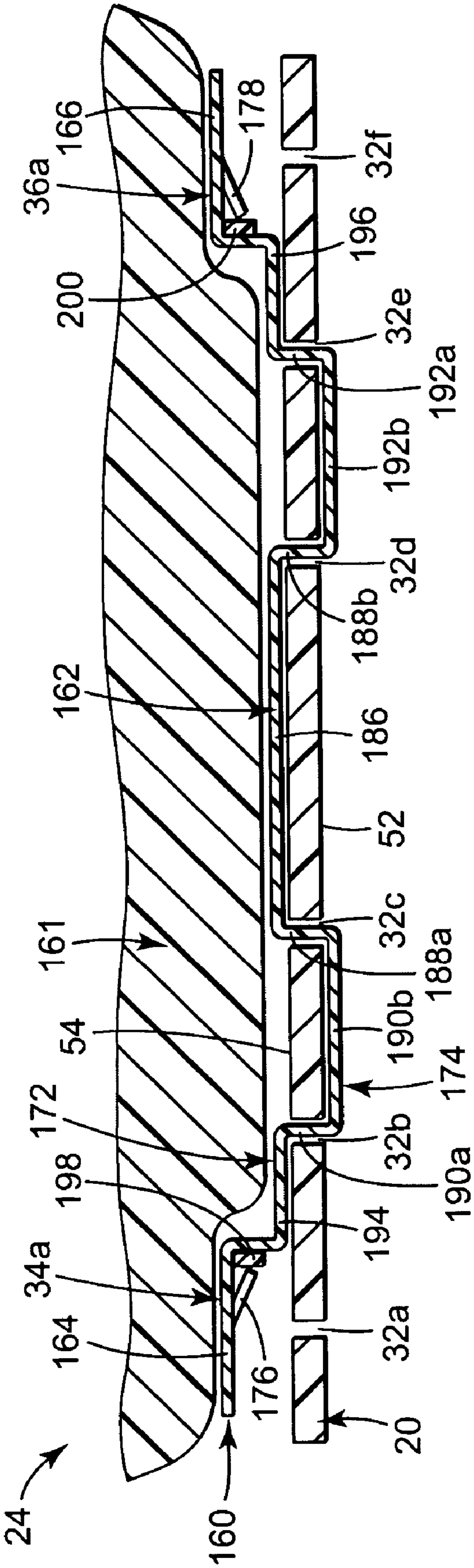
FIG. 18 is a schematic cross-sectional view of the waist-mounted respiratory component system, taken along line A-A of FIG. 4, and including the respiratory component mounting clip of FIG. 15.

FIG. 18 is a cross-sectional view of the waist-mounted respiratory component system 24, taken along line A-A of FIG. 4, showing the respiratory component mounting clip 160 and an alternative respiratory component 161 mounted to the belt 20. An example of a suitable respiratory component for use with the mounting clip 160 is DUSTMASTER brand respirator from 3M Company of St. Paul, Minn. The intermediate portion 162 of the clip 160 is woven through the mounting slots 32 of the belt 20, whereby the free ends 164, 166 project from the inner surface 54 of the belt 20. In the embodiment shown in FIG. 18, four of the mounting slots 32*b*, 32*c*, 32*d* and 32*e* receive walls 190*a*, 188*a*, 192*a* and 188*b*, respectively, of the intermediate portion 162 of the clip 160. Between each adjacent mounting slot 32*a*-32*f*, one of the ledges 194, 190*b*, 186, 192*b* and 196 of the two faces (172, 174) of the clip 160 aligns against either the outer face 52 or the inner face 54 of the belt 20.

The respiratory component 161 includes first and second openings 34*a* and 36*a* for removably receiving the free ends 164, 166 of the clip 160. The respiratory component 161 also includes first and second opposed detent surfaces 198, 200 adjacent the first and second clip openings 34, 36, respectively. The openings 34*a* and 36*a* of the respiratory component 161 receive the free ends 164, 166 of the clip 160 whereby the detent tabs 176, 178 of the clip 160 form a locking engagement with the detent surfaces 198, 200 of the respiratory component 161. To attach or remove the respiratory component 12 from the belt 20, the free ends 164, 166 of the clip 160 are inserted into or removed from the clip openings 34, 36 in the respiratory component 161. Detent tabs 176, 178 are pressed towards the second surface 172 of the clip 160 to facilitate insertion and removal of the clip from the respiratory component. At least the free ends 164, 166 of the clip 160 are flexibly resilient to accommodate insertion and removal to and from the clip openings 34, 36 of the respiratory component 161. The intermediate portion 162 of the clip 160 is sufficiently flexible to weave through the mounting slots 32 of the belt 20.

FIGS. 19-32 present alternative mounting clip designs for use with the belt 20, which are formed for use with different respiratory components or to allow different modes of assembly of the relative components.

Figure 19:
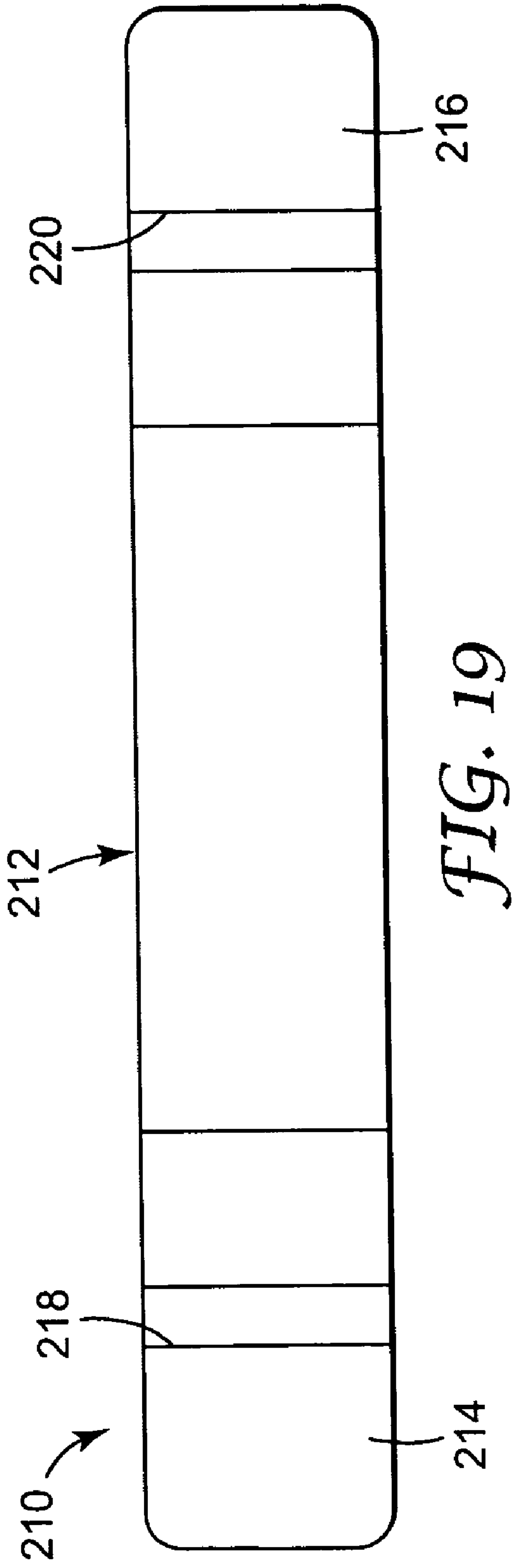
FIG. 19 is a top view of a further embodiment of a respiratory component mounting clip.
Figure 20:
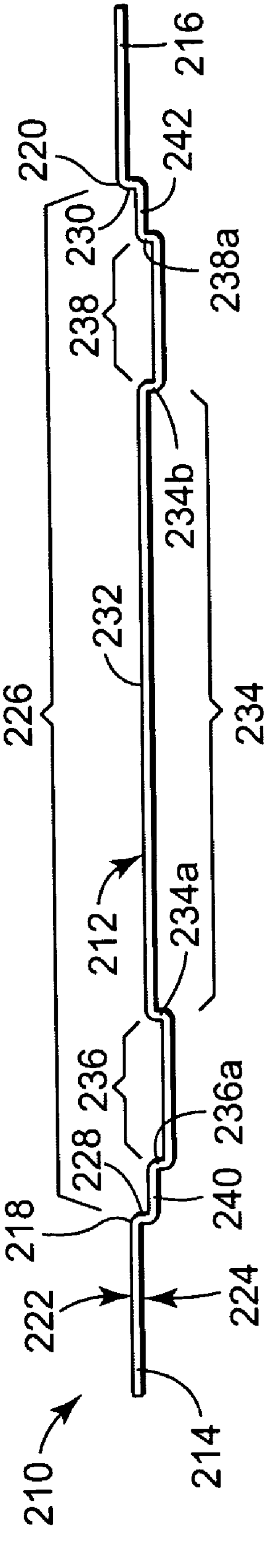
FIG. 20 is a side view of the respiratory component mounting clip of FIG. 19.

FIGS. 19 and 20 are top and side views, respectively, of a further embodiment of a respiratory component mounting clip 210. The mounting clip 210 shown in FIGS. 19 and 20 is similar to the mounting clip 160 shown in FIGS. 15-18, but does not include biased detent tabs. The mounting clip 210 includes an intermediate portion 212 and two spaced apart free ends 214, 216 connected to the intermediate portion 212. The intermediate portion 212 extends between a first shoulder 218 and a second shoulder 220, while the first and second free ends 214, 216 extend from the first and second shoulders 218, 220, respectively. The free ends 214, 216 are aligned to extend in generally opposite directions. The mounting clip 210 has a first surface 22 and a second surface 224.

The first surface 22 of the intermediate portion 212 defines a channel 226 extending between a first outer wall 228 and a second outer wall 230. The channel 226 includes a stepped portion 232 extending towards the first surface 222 and defining a second channel 234 on the second surface 224 of the mounting clip 210. A depth of the first channel 226 (defined by walls 228 and 230) is greater than a depth of the second channel 234 (defined by walls 234*a* and 234*b*). First and second subchannels 236, 238 formed in the channel 226 extend towards the second surface 224 and are defined on the first surface 222 of the mounting clip 210. A depth of each subchannel 236 (defined by walls 236*a* and 234*a*) and 238 (defined by walls 238*a* and 234*b*) is substantially equal to the depth of the second channel 234. First and second ledges 240, 242 extend between the first and second subchannels 236, 238 and the first and second outer walls 228, 230, respectively.

To attach the respiratory component 12 to the belt 20, this embodiment of the mounting clip 210 is used in the same fashion as those discussed above with respect to FIGS. 6-9 and 15-18. The intermediate portion 210 of the clip 212 is woven through suitable mounting slots 32 of the belt 20, whereby the free ends 214, 216 project from the inner surface 54 of the belt 20. Between mounting slots 32, one of the two faces (222, 224) of the clip 210 aligns against either the outer face 52 or the inner face 54 of the belt 20. To attach or remove the respiratory component 12 from the belt 20, the free ends 241, 216 of the clip 210 are inserted into or removed from the clip openings 34, 36 in the respiratory component 12.

Figure 21:
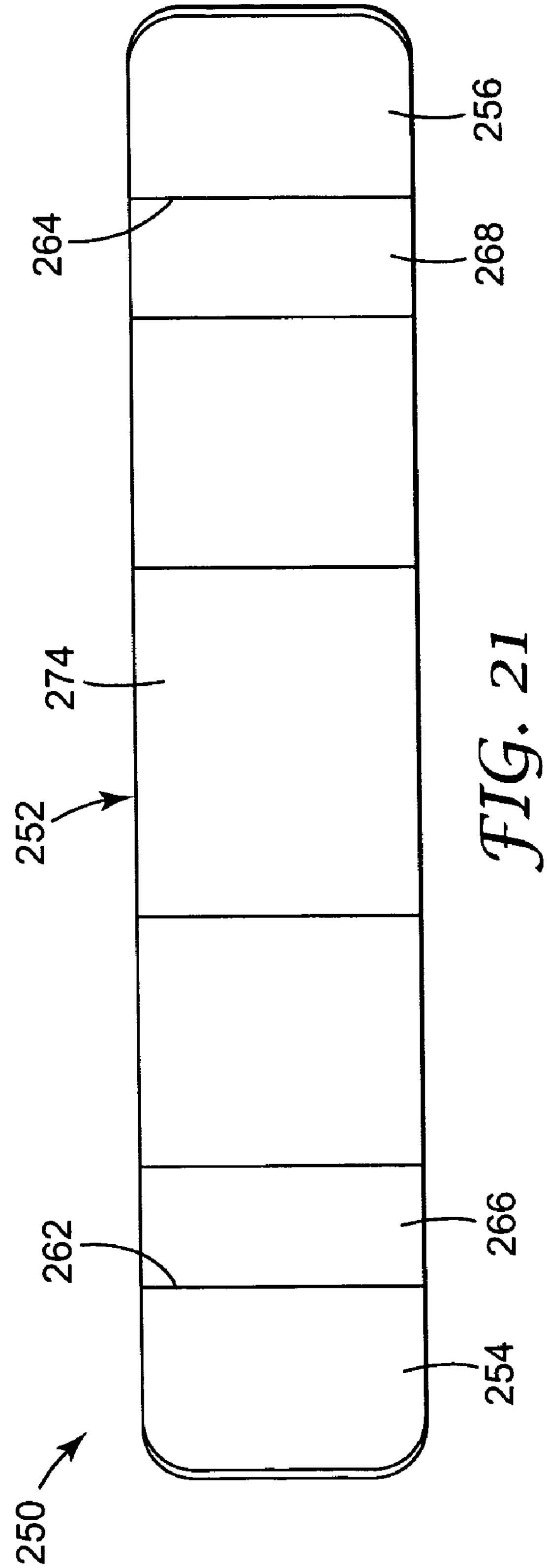
FIG. 21 is a top view of a further embodiment of a respiratory component mounting clip.
Figure 22:
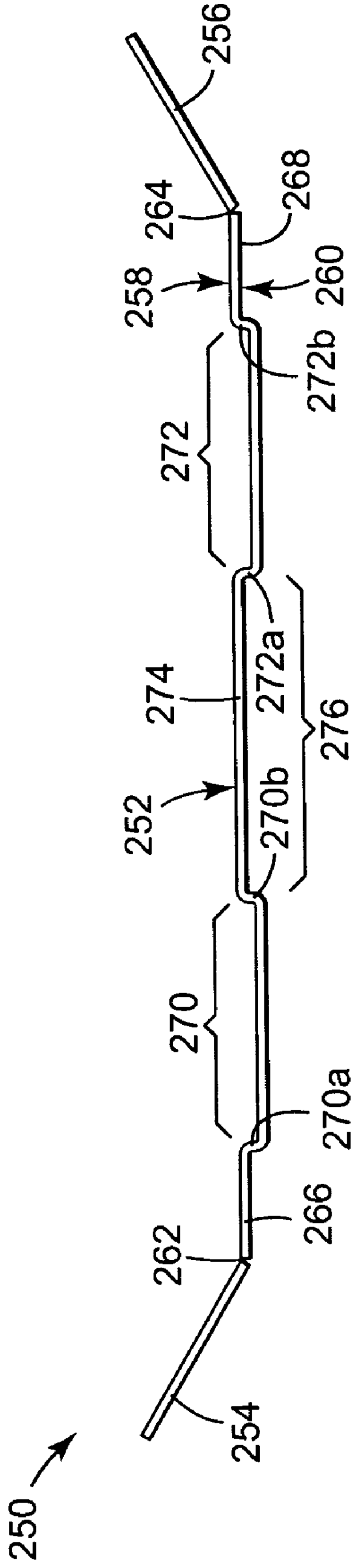
FIG. 22 is a side view of the respiratory component mounting clip of FIG. 21.

FIGS. 21 and 22 are top and side views, respectively, of a further embodiment of a respiratory component mounting clip 250. The mounting clip 250 includes an intermediate portion 252, two spaced apart first and second free ends 254, 256 connected to the intermediate portion 252, a first surface 258 and a second surface 260. The intermediate portion 252 extends between a first living hinge 262 and a second living hinge 264, which connect the intermediate portion 252 to the first and second free ends 254, 256, respectively.

The intermediate portion 252 includes first and second ledges 266, 268 that extend from the first and second hinges 262, 264, respectively. The first surface 258 of the intermediate portion 252 defines first and second channels 270, 272 that are positioned adjacent the first and second ledges 266, 268, respectively, and a stepped portion 274 connects the first and second channels 270, 272. The stepped portion 274 extends towards the first surface 258 and defines a third channel 276 on the second surface 260 of the mounting clip 250. A depth of the first channel 270 (defined by walls 270*a* and 270*b*) and the second channel 272 (defined by walls 272*a* and 272*b*) is substantially equal to a depth of the third channel 276 (defined by walls 270*b* and 272*a*).

To attach the respiratory component 12 to the belt 20, this embodiment of the mounting clip 250 is used in the same fashion as those discussed above with respect to FIGS. 6-9 and 15-18. The intermediate portion 252 of the clip 250 is woven through suitable mounting slots 32 of the belt 20, whereby the free ends 254, 256 project from the inner surface 54 of the belt 20. Between mounting slots 32, one of the two faces (258, 260) of the clip 250 aligns against either the outer face 52 or the inner face 54 of the belt 20. To attach or remove the respiratory component 12 from the belt 20, the free ends 254, 256 of the clip 250 are inserted into or removed from the clip openings 34, 36 in the respiratory component 12.

Figure 23:
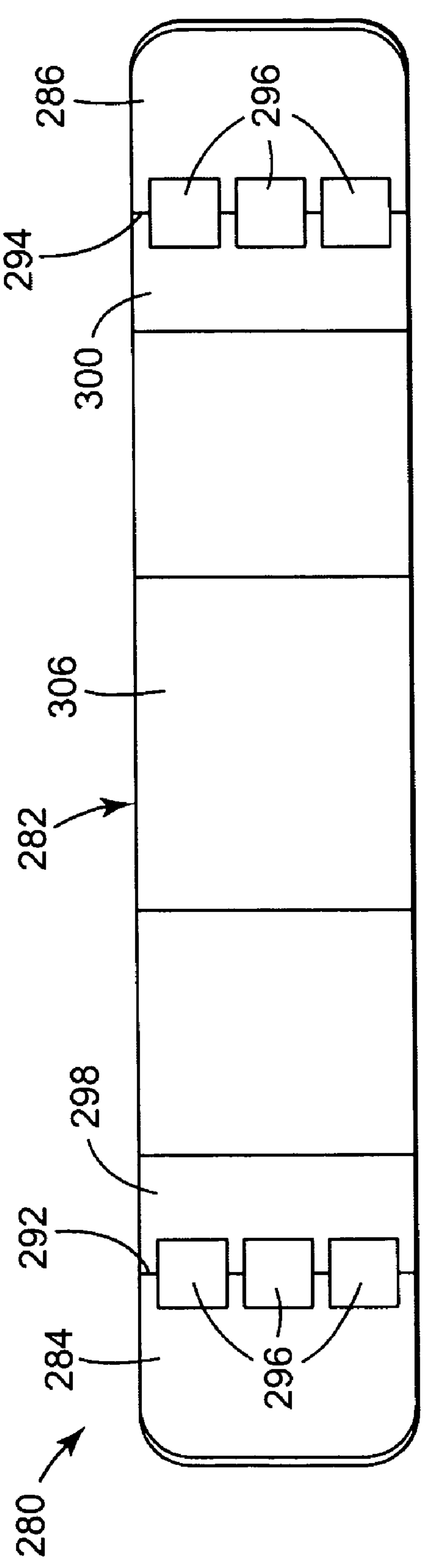
FIG. 23 is a top view of a further embodiment of a respiratory component mounting clip.
Figure 24:
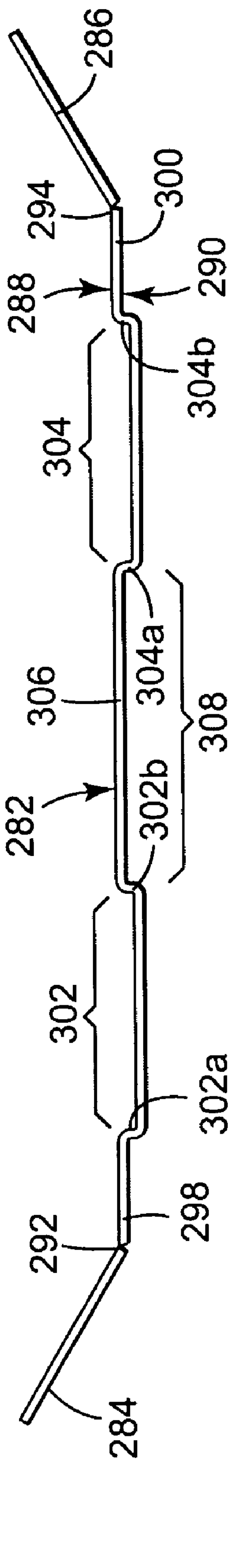
FIG. 24 is a side view of the respiratory component mounting clip of FIG. 23.

FIGS. 23 and 24 are top and side views, respectively, of a further embodiment of a respiratory component mounting clip 280. The mounting clip 280 includes an intermediate portion 282, two spaced apart first and second free ends 284, 286 connected to the intermediate portion 282, a first surface 288 and a second surface 290. The intermediate portion 282 extends between a first living hinge 292 and a second living hinge 294, which connect the intermediate portion 282 to the first and second free ends 284, 286, respectively. The mounting clip 280 of FIGS. 23 and 24 is the same as the embodiment shown in FIGS. 21 and 22, however, there is a difference between the living hinges 294, 294. The first and second hinges 292, 294 include a number of openings 296 to increase the flexibility of the free ends 284, 286 with respect to the intermediate portion 282.

The intermediate portion 282 includes first and second ledges 298, 300 that extend from the first and second hinges 292, 294, respectively. The first surface 288 of the intermediate portion 282 defines first and second channels 302, 304 that are positioned adjacent the first and second ledges 289, 300, respectively. A stepped portion 306 connects the first and second channels 302, 304 and extends towards the first surface 288 to define a third channel 308 on the second surface 290 of the mounting clip 280. A depth of the first channel 302 (defined by walls 302*a* and 302*b*) and the second channel 304 (defined by walls 304*a* and 304*b*) is substantially equal to a depth of the third channel 308 (defined by walls 302*b* and 304*a*). To attach the respiratory component 12 to the belt 20, this embodiment of the mounting clip 280 is used in the same fashion as that discussed above with respect to FIGS. 21 and 22.

Figure 25:
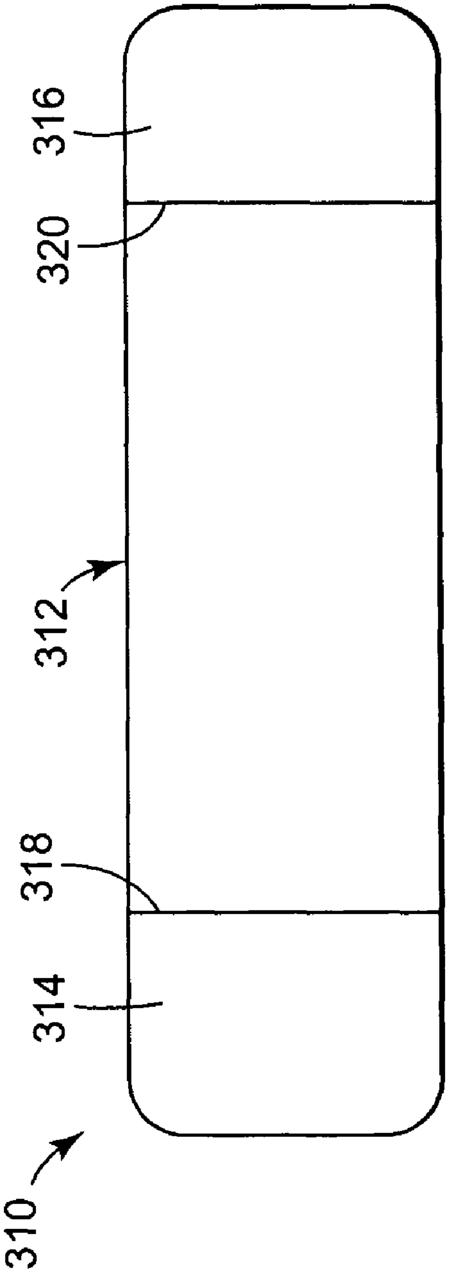
FIG. 25 is a top view of a further embodiment of a respiratory component mounting clip.
Figure 26:
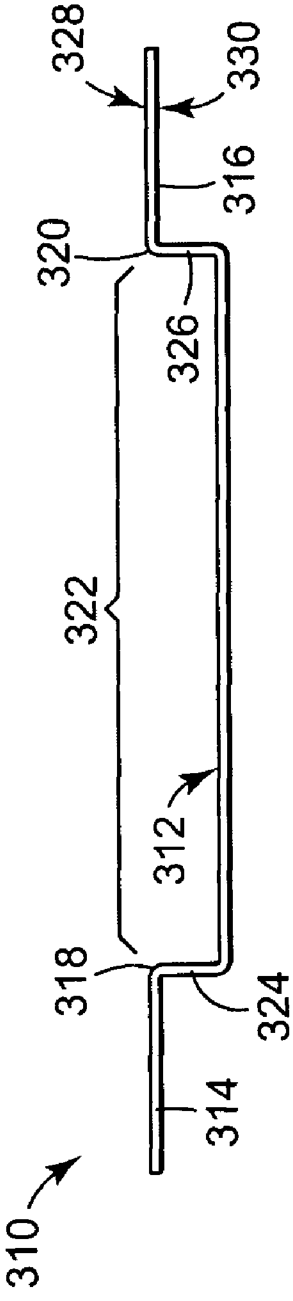
FIG. 26 is a side view of the respiratory component mounting clip of FIG. 25.

FIGS. 25 and 26 are top and side views, respectively, of a further embodiment of a respiratory component mounting clip 310. The mounting clip 310 includes an intermediate portion 312 and two spaced apart free ends 314, 316 connected to the intermediate portion 312. The intermediate portion 312 extends between a first shoulder 318 and a second shoulder 320 and includes a channel 322 extending between first and second outer walls 324, 326. The first and second free ends 314, 316 extend from the first and second shoulders 318, 320, respectively and are aligned to extend in generally opposite directions. The mounting clip 310 has a first surface 328 and a second surface 330.

To attach the respiratory component 12 to the belt 20, this embodiment of the mounting clip 310 is used in the same fashion as those discussed above with respect to FIGS. 6-9 and 15-18. The intermediate portion 312 of the clip 310 is woven through suitable mounting slots 32 of the belt 20, whereby the free ends 314, 316 project from the inner surface 54 of the belt 20. Between mounting slots 32, one of the two faces (328, 330) of the clip 30 aligns against either the outer face 52 or the inner face 54 of the belt 20. To attach or remove the respiratory component 12 from the belt 20, the free ends 314, 316 of the clip 310 are inserted into or removed from the clip openings 34, 36 in the respiratory component 12.

Figure 27:
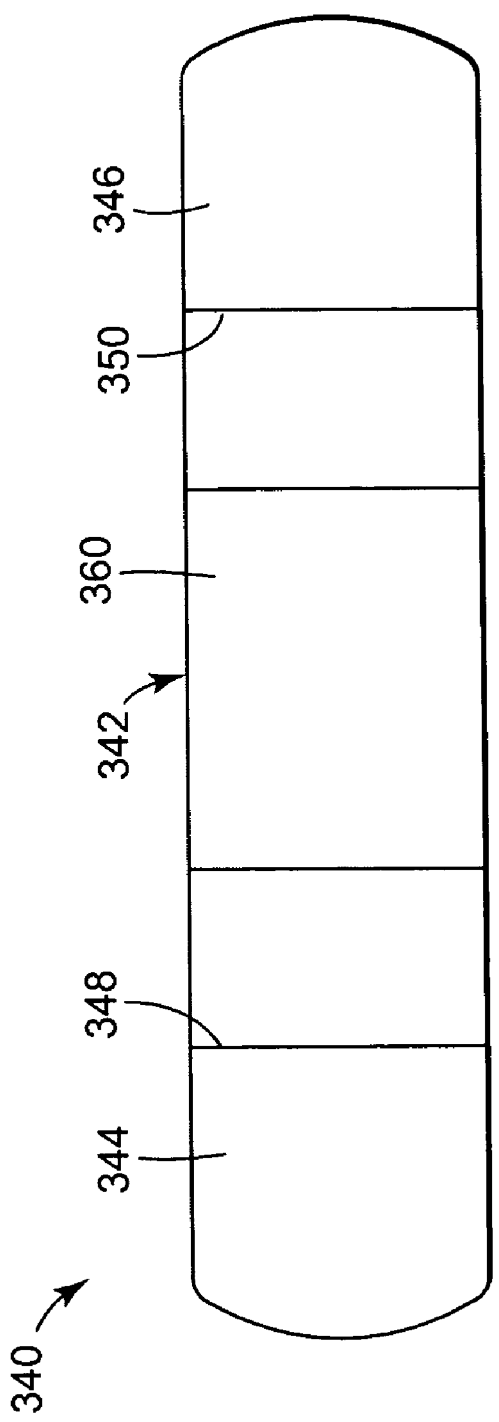
FIG. 27 is a top view of a further embodiment of a respiratory component mounting clip.
Figure 28:
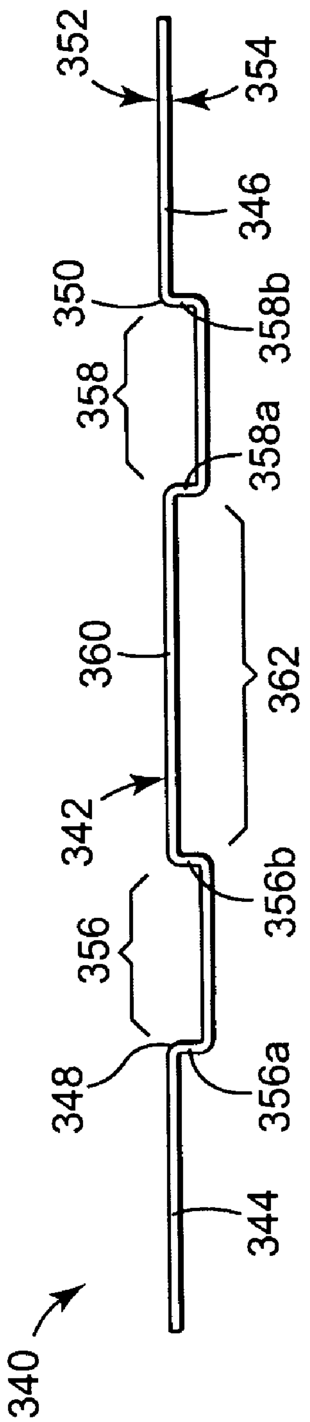
FIG. 28 is a side view of the respiratory component mounting clip of FIG. 27.

FIGS. 27 and 28 are top and side views, respectively, of a further embodiment of a respiratory component mounting clip 340. The mounting clip 340 includes an intermediate portion 342 and two spaced apart free ends 344, 346 connected to the intermediate portion 342. The intermediate portion 342 extends between a first shoulder 348 and a second shoulder 350, while the first and second free ends 344, 346 extend from the first and second shoulders 348, 350, respectively. The free ends 344, 346 are aligned to extend in generally opposite directions. The mounting clip 340 has a first surface 352 and a second surface 354.

The first surface 352 of the intermediate portion 342 defines first and second channels 356, 358 that are positioned adjacent the first and second shoulders 348, 350, respectively. A stepped portion 360 connects the first and second channels 356, 358 and extends towards the first surface 352 to define a third channel 362 on the second surface 354 of the mounting clip 350. A depth of the first channel (defined by walls 356*a* and 356*b*) and the second channel 358 (defined by walls 358*a* and 358*b*) is substantially equal to a depth of the third channel 362 (defined by walls 356*b* and 358*a*).

To attach the respiratory component 12 to the belt 20, this embodiment of the mounting clip 340 is used in the same fashion as those discussed above with respect to FIGS. 6-9 and 15-18. The intermediate portion 342 of the clip 340 is woven through suitable mounting slots 32 of the belt 20, whereby the free ends 344, 346 project from the inner surface 54 of the belt 20. Between mounting slots 32, one of the two faces (352, 354) of the clip 340 aligns against either the outer face 52 or inner face 54 of the belt 20. To attach or remove the respiratory component 12 from the belt 20, the free ends 344, 346 of the clip 340 are inserted into or removed from the clip openings 34, 36 in the respiratory component 12.

Figure 29:
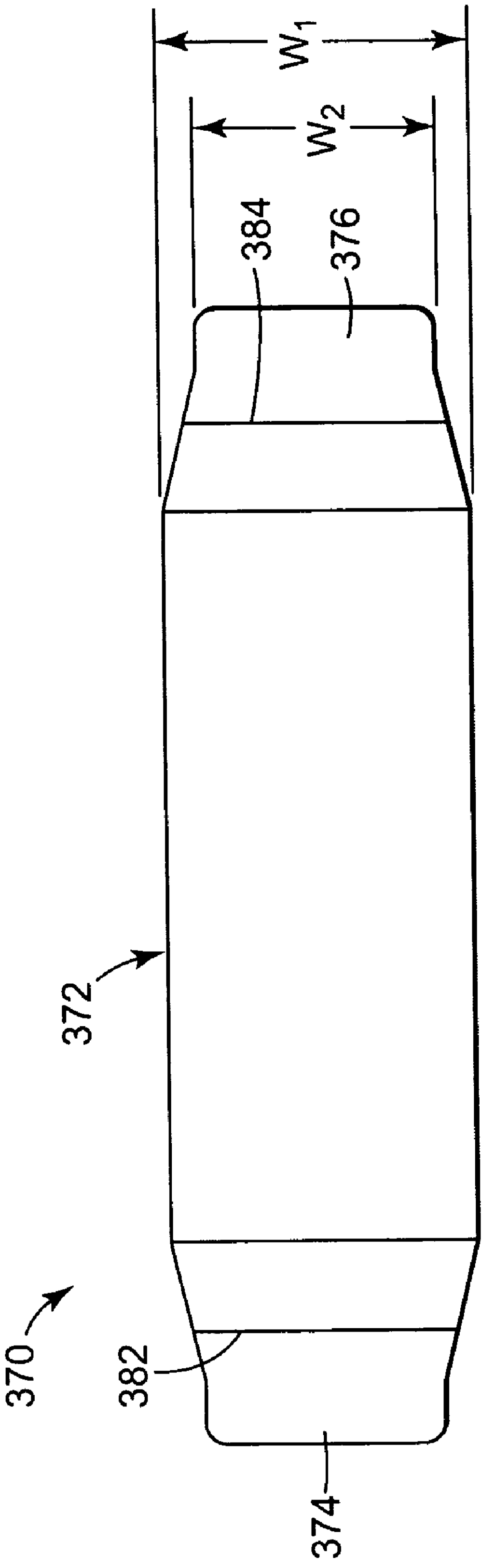
FIG. 29 is a top view of a further embodiment of a respiratory component mounting clip.
Figure 30:
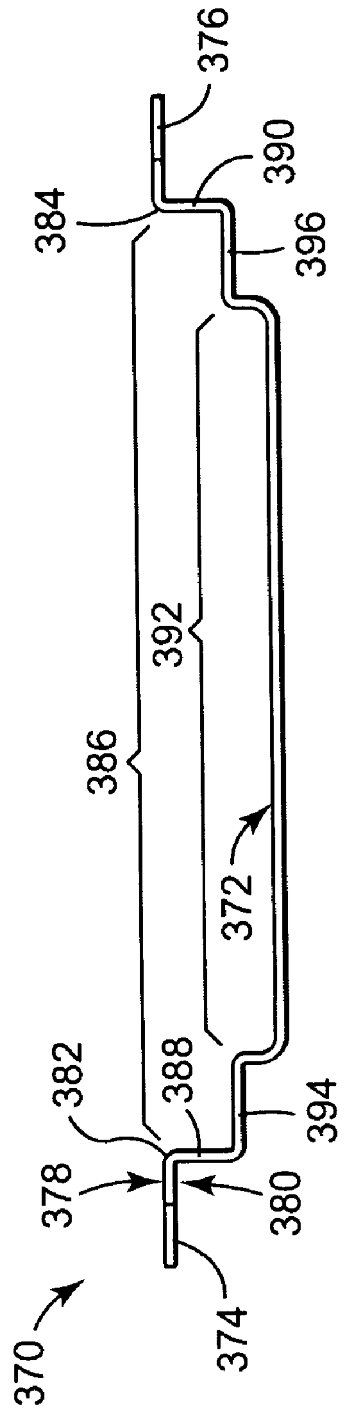
FIG. 30 is a side view of the respiratory component mounting clip of FIG. 29.

FIGS. 29 and 30 are top and side views, respectively, of a further embodiment of a respiratory component mounting clip 370. The mounting clip 370 includes an intermediate portion 372, two spaced apart free ends 374, 376 connected to the intermediate portion 372, a first surface 378 and a second surface 380. The intermediate portion 372 extends between a first shoulder 382 and a second shoulder 384, while the first and second free ends 374, 376 extend from the first and second shoulders 382, 384, respectively. The free ends 374, 376 are aligned to extend in generally opposite directions. A portion of each free end tapers inward towards a longitudinal axis of the clip such that a width $W_1$ of the free ends 374, 376 is smaller than a width $W_2$ of the intermediate portion 372.

The first surface 378 of the intermediate portion 372 defines a channel 386 extending between a first outer wall 388 and a second outer wall 390. A subchannel 392 is defined in the channel 386 and first and second ledges 394, 396 connect the subchannel 392 to the first and second outer walls 388, 390, respectively.

To attach the respiratory component 12 to the belt 20, this embodiment of the mounting clip 370 is used in the same fashion as those discussed above with respect to FIGS. 6-9 and 15-18. The intermediate portion 372 of the clip 370 is woven through suitable mounting slots 32 of the belt 20, whereby the free ends 374, 376 project from the inner surface 54 of the belt 20. Between mounting slots 32, one of the two faces (378, 380) of the clip 370 aligns against either the outer face 52 or the inner face 54 of the belt 20. To attach or remove the respiratory component 12 from the belt 20, the free ends 274, 276 of the clip 270 are inserted into or removed from the clip openings 34, 36 in the respiratory component 12.

Figure 31:
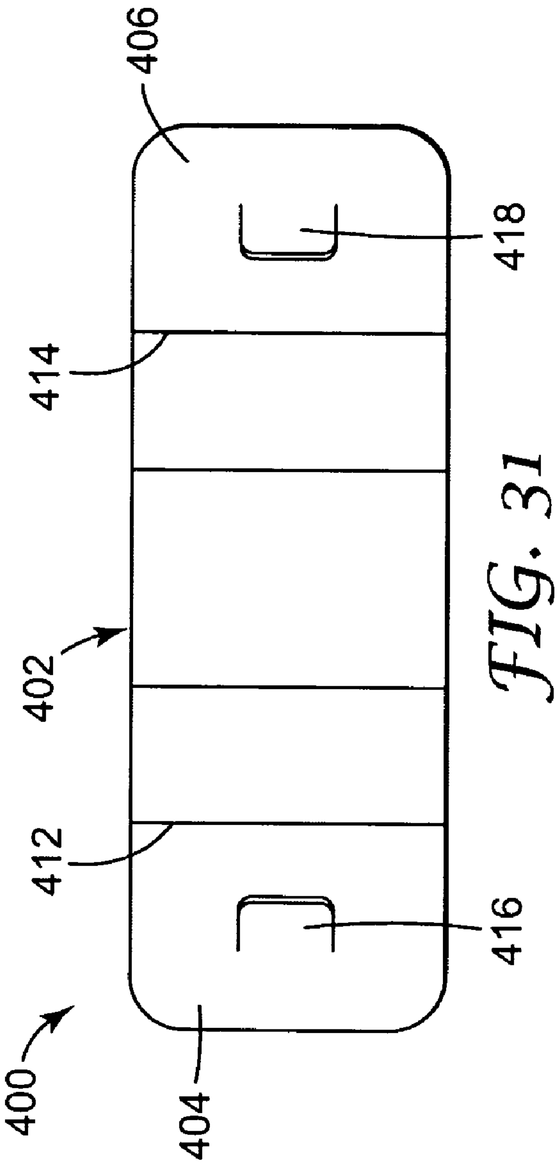
FIG. 31 is a top view of a further embodiment of a respiratory component mounting clip.
Figure 32:
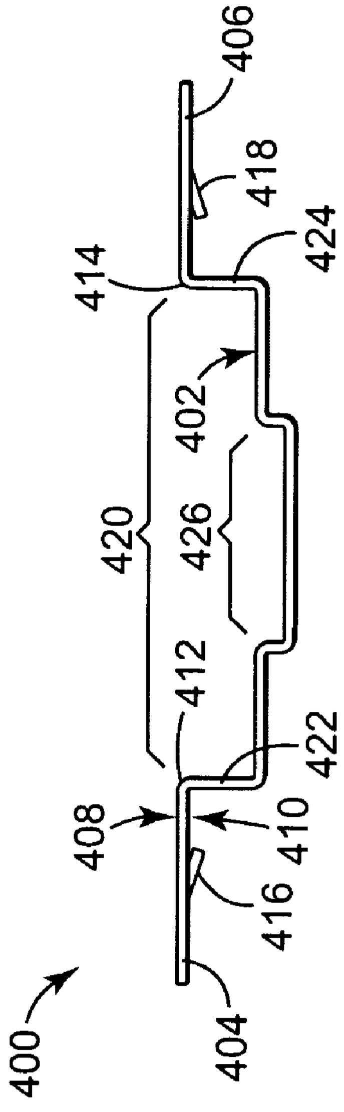
FIG. 32 is a side view of the respiratory component mounting clip of FIG. 31.

FIGS. 31 and 32 are top and side views, respectively, of a further embodiment of a respiratory component mounting clip 400. The mounting clip 400 includes an intermediate portion 402, two spaced apart free ends 404, 406 connected to the intermediate portion 402, a first surface 408 and a second surface 410. The intermediate portion 402 extends between a first shoulder 412 and a second shoulder 414, while the first and second free ends 404, 406 extend from the first and second shoulders 412, 414, respectively. The free ends 404, 406 are aligned to extend in generally opposite directions. The first and second free ends 404, 406 of the mounting clip 400 include first and second biased detent tabs 416, 418 extending generally downwardly and inwardly from the second surface 408 of the mounting clip 400.

The first surface 408 of the intermediate portion 402 defines a channel 420 extending between a first outer wall 422 and a second outer wall 424. A subchannel 426 is defined in the channel 420 and first and second ledges 428, 430 connect the subchannel 426 to the first and second outer walls 422, 424, respectively.

To attach the respiratory component 12 to the belt 20, this embodiment of the mounting clip 400 is used in the same fashion as those discussed above with respect to FIGS. 6-9 and 15-18. The intermediate portion 402 of the clip 400 is woven through suitable mounting slots 32 of the belt 20, whereby the free ends 404, 406 project from the inner surface 54 of the belt 20. Between mounting slots 32, one of the two faces (408, 410) of the clip 400 aligns against either the outer face 52 or inner face 54 of the belt 20. To attach or remove the respiratory component 12 from the belt 20, the free ends 404, 406 of the clip 400 are inserted into or removed from the clip openings 34, 36 in the respiratory component 12.

The respiratory protection system is generally used in hazardous and contaminated environments, thereby requiring that the mounting assemblies, and other components, be readily decontaminatible such that they may be reused in further applications. In addition, at least the free ends 28, 30 of the mounting clip 18 are flexibly resilient to accommodate insertion and removal to and from respiratory component clip openings 34, 36. The intermediate portion 26 of the clip 18 is sufficiently flexible to weave through the mounting slots 32 of the belt 20. The mounting clips are formed from a polypropylene, nylon or polyethylene, for example, by injection molding or vacuum forming. An example of a suitable polypropylene is FINA 4460 from Atofina (Houston, Tex.). Each mounting clip has a thickness of approximately 2.2 mm.

In further embodiments of the respiratory component system, the belt 20 includes sufficient mounting slots 32 for accommodating more than one mounting clip 18, and thereby facilitating the attachment of more than one respiratory component 12. Rather than just attaching a respiratory component at the back section 42 of the belt 20, additional components may attached along the entire outer perimeter of the belt 20. In addition, the alignment of the free ends 28, 30 of a mounting clip 18 may be different from one clip to another to accommodate differing orientations of connector receptacles 34, 36 on the respiratory components.

Although the present invention has been described with reference to several embodiments, workers skilled in the art will recognize that changes may be made in form and detail without departing from the spirit and scope of the invention. For example, a multitude of mounting assemblies including an intermediate portion and two spaced apart free ends are possible for attaching a respiratory component to a user-wearable support member. Thus, the invention is not limited to the embodiments disclosed and described above, and additional embodiments may include fewer or more channels, stepped portions, ledges, detent tabs and/or hinges.

The invention claimed is:

1. A respiratory component mounting assembly comprising:

a respiratory component having at least two spaced apart connector receptacles therein;

a mounting clip having at least two spaced apart free ends which are at least partially received within the connector receptacles of the respiratory component; and a user-wearable respiratory component support member configured to be disposed around a user's waist and having at least two slots therein, wherein an intermediate portion of the mounting clip between its free ends is received in those slots for affixing the respiratory component to the respiratory component support member.

2. The respiratory component mounting assembly of claim 1 wherein the support member has four generally parallel slots therein, and the intermediate portion of the mounting clip is received in each of those slots.

3. The respiratory component mounting assembly of claim 2 wherein the support member has an inner face and an outer face, wherein the intermediate portion of the mounting clip has a first surface and a second surface, and wherein between each pair of adjacent slots in the support member, one of the faces of the mounting clip is aligned generally against one of the faces of the support member.

4. The respiratory component mounting assembly of claim 1, and further comprising:

the respiratory component being one of a plurality of respiratory components, with each respiratory component having at least two spaced apart connector receptacles therein, wherein the orientations of the connector receptacles from one respiratory component to another are different; and the mounting clip being one of a plurality of mounting clips, each mounting clip having at least two spaced apart free ends, wherein the alignments of the free ends from one mounting clip to another are different to accommodate the different orientations of connector receptacles on the respiratory components.

5. The respiratory component mounting assembly of claim 1, wherein the free ends of the mounting clip are aligned to extend in generally opposite directions.

6. The respiratory component mounting assembly of claim 1 wherein the free ends of the mounting clip are aligned to extend toward each other.

7. The respiratory component mounting assembly of claim 6 wherein the mounting clip includes at least one living hinge between each free end and the intermediate portion of the mounting clip.

8. The respiratory component mounting assembly of claim 1 wherein each free end of the mounting clip has a biased detent tab thereon for locking engagement with an opposing detent surface adjacent its respective connector receptacle on the respiratory component.

9. The respiratory component mounting assembly of claim 1 wherein the support member is a belt.

10. The respiratory component mounting assembly of claim 9 wherein the belt has a main portion which extends around the sides and back of a user, and a connected buckle portion which extends across the front of a user, and wherein the slots are on a back side in the main portion of the belt.

11. The respiratory component mounting assembly of claim 10 wherein the buckle portion of the belt is detachable from the main portion.

12. The respiratory component mounting assembly of claim 1 wherein the slots are generally parallel.

13. The respiratory component mounting assembly of claim 1 wherein the slots are generally vertically aligned.

14. The respiratory component mounting assembly of claim 1 wherein at least the free ends of the mounting clip are flexibly resilient.

15. The respiratory component mount assembly of claim 1, wherein each free end is removably received within its respective connector receptacle of the respiratory component.

16. The respiratory component assembly of claim 1 wherein the intermediate portion of the mounting clip is removably received in the slots of the respiratory component support member.

17. The respiratory component assembly of claim 1 wherein the mounting clip is formed from a polypropylene.

18. A method of mounting a respiratory component to a user-wearable respiratory support member comprises:

providing a respiratory component comprising at least two spaced apart connector receptacles;

providing a support member configured to be disposed around a user's waist, the support member comprising at least two slots;

providing a mounting clip having an intermediate portion and two spaced apart free ends projecting therefrom;

inserting the intermediate portion of the mounting clip into the clip openings on the respiratory component, with the free ends of the mounting clip projecting from one side of the respiratory component; and inserting the free ends of the mounting clip into the slots of the support member.

19. The method of claim 18, and further comprising: reinforcing the slots in the support member.

* * * * *